(12) United States Patent
Orban, III

(10) Patent No.: US 7,743,958 B2
(45) Date of Patent: *Jun. 29, 2010

(54) END-TO-END ANASTOMOSIS INSTRUMENT AND METHOD FOR PERFORMING SAME

(75) Inventor: Joseph P. Orban, III, Norwalk, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 440 days.

This patent is subject to a terminal disclaimer.

(21) Appl. No.: 11/429,505

(22) Filed: May 5, 2006

(65) Prior Publication Data

US 2007/0062999 A1     Mar. 22, 2007

Related U.S. Application Data

(63) Continuation of application No. 10/993,544, filed on Nov. 19, 2004, now Pat. No. 7,059,510, which is a continuation of application No. PCT/US03/18295, filed on May 30, 2003, which is a continuation of application No. 10/160,460, filed on May 31, 2002, now Pat. No. 6,769,594.

(51) Int. Cl.
*A61B 17/068* (2006.01)

(52) U.S. Cl. .................. 227/176.1; 227/19; 606/219

(58) Field of Classification Search ............ 227/19, 227/176.1, 175.1, 178.1, 179.1; 606/219, 606/153

See application file for complete search history.

(56) References Cited

U.S. PATENT DOCUMENTS

| | | | |
|---|---|---|---|
| 2,968,041 A | 1/1961 | Skold | |
| 3,152,336 A | 10/1964 | Brady | |
| 3,232,089 A | 2/1966 | Samuels et al. | |
| 3,254,650 A | 6/1966 | Collito | |
| 3,297,033 A | 1/1967 | Schmitt et al. | |
| 3,366,301 A | 1/1968 | Mallina | |
| 3,477,423 A | 11/1969 | Griffith | |
| 3,496,939 A | 2/1970 | Odiaga et al. | |
| 3,519,187 A | 7/1970 | Kapitanov et al. | |
| 3,575,038 A | 4/1971 | Mallett | |
| 3,741,025 A | 6/1973 | Russell | |
| 3,771,526 A | 11/1973 | Rudie | |

(Continued)

FOREIGN PATENT DOCUMENTS

EP        384647  A1    2/1990

(Continued)

OTHER PUBLICATIONS

International Search Report—EPO 97112634—Dec. 18, 1997.

(Continued)

*Primary Examiner*—Scott A. Smith

(57) ABSTRACT

A surgical instrument for performing an end-to-end anastomosis of first and second luminal structures includes a housing having an actuator attached thereto and a selectively removable loading unit attached to a distal end of the housing which supports any array of surgical fasteners at a distal end thereof. The surgical fasteners are simultaneously deformable upon activation of the actuator such that a distal end of each surgical fastener secures each end of each luminal structure to complete the end-to-end anastomosis wherein the resulting eversion is exterior to the luminal structures.

15 Claims, 26 Drawing Sheets

U.S. PATENT DOCUMENTS

| | | | |
|---|---|---|---|
| 3,776,237 A | 12/1973 | Hill et al. | |
| 3,856,016 A | 12/1974 | Davis | |
| 3,908,662 A | 9/1975 | Razlov et al. | |
| 3,954,108 A | 5/1976 | Davis | |
| 3,974,835 A | 8/1976 | Hardy, Jr. | |
| 4,018,228 A | 4/1977 | Goosen | |
| 4,152,920 A | 5/1979 | Green | |
| 4,166,466 A | 9/1979 | Jarvik | |
| 4,182,339 A | 1/1980 | Hardy, Jr. | |
| 4,201,314 A | 5/1980 | Samuels et al. | |
| 4,216,776 A | 8/1980 | Downie et al. | |
| 4,242,902 A | 1/1981 | Green | |
| 4,299,224 A | 11/1981 | Noiles | |
| 4,316,468 A | 2/1982 | Klieman et al. | |
| 4,321,002 A | 3/1982 | Froehlich | |
| 4,325,376 A | 4/1982 | Klieman et al. | |
| 4,350,160 A | 9/1982 | Kolesov et al. | |
| 4,368,736 A | 1/1983 | Kaster | |
| 4,372,316 A | 2/1983 | Blake, III et al. | |
| 4,408,603 A | 10/1983 | Blake, III et al. | |
| 4,412,539 A | 11/1983 | Jarvik | |
| 4,425,915 A | 1/1984 | Ivanov | |
| 4,430,997 A | 2/1984 | DiGiovanni et al. | |
| 4,432,925 A | 2/1984 | Holtzberg et al. | |
| 4,452,376 A | 6/1984 | Klieman et al. | |
| 4,466,436 A | 8/1984 | Lee | |
| 4,467,804 A | 8/1984 | Hardy et al. | |
| 4,476,863 A | 10/1984 | Kanshin et al. | |
| 4,480,640 A | 11/1984 | Becht | |
| D276,650 S | 12/1984 | Green et al. | |
| 4,488,543 A | 12/1984 | Tornier | |
| 4,493,317 A | 1/1985 | Klaue | |
| 4,503,848 A | 3/1985 | Caspar et al. | |
| 4,509,518 A | 4/1985 | McGarry et al. | |
| 4,522,207 A | 6/1985 | Klieman et al. | |
| 4,534,351 A | 8/1985 | Rothfuss et al. | |
| 4,552,148 A | 11/1985 | Hardy et al. | |
| 4,586,503 A | 5/1986 | Kirsch et al. | |
| 4,598,711 A | 7/1986 | Deniega | |
| 4,611,595 A | 9/1986 | Klieman et al. | |
| 4,616,650 A | 10/1986 | Green et al. | |
| 4,671,445 A | 6/1987 | Barker et al. | |
| 4,700,703 A | 10/1987 | Resnick et al. | |
| 4,708,141 A | 11/1987 | Inoue et al. | |
| 4,712,549 A | 12/1987 | Peters et al. | |
| 4,752,024 A | 6/1988 | Green et al. | |
| 4,759,364 A | 7/1988 | Boebel | |
| 4,766,898 A | 8/1988 | Hardy et al. | |
| 4,809,695 A | 3/1989 | Gwathmey et al. | |
| 4,821,939 A | 4/1989 | Green | |
| 4,872,874 A | 10/1989 | Taheri | |
| 4,874,122 A | 10/1989 | Froelich et al. | |
| 4,893,622 A | 1/1990 | Green et al. | |
| 4,899,744 A | 2/1990 | Fujitsuka et al. | |
| 4,907,591 A | 3/1990 | Vasconcellos et al. | |
| 4,917,114 A | 4/1990 | Green et al. | |
| 4,929,240 A | 5/1990 | Kirsch et al. | |
| 4,930,674 A | 6/1990 | Barak | |
| 4,931,057 A | 6/1990 | Cummings et al. | |
| 4,957,499 A | 9/1990 | Lipatov et al. | |
| 4,979,954 A | 12/1990 | Gwathmey et al. | |
| 4,983,176 A | 1/1991 | Cushman et al. | |
| 5,025,779 A | 6/1991 | Bugge | |
| 5,030,226 A | 7/1991 | Green et al. | |
| 5,057,111 A | 10/1991 | Park | |
| 5,104,395 A | 4/1992 | Thornton et al. | |
| 5,108,395 A | 4/1992 | Laurain | |
| 5,112,343 A | 5/1992 | Thornton | |
| 5,122,150 A | 6/1992 | Puig | |
| 5,127,912 A | 7/1992 | Ray et al. | |
| 5,129,913 A | 7/1992 | Ruppert | |
| 5,147,361 A | 9/1992 | Ojima et al. | |
| 5,188,638 A | 2/1993 | Tzakis | |
| 5,192,288 A | 3/1993 | Thompson et al. | |
| 5,192,294 A | 3/1993 | Blake, III | |
| 5,211,649 A | 5/1993 | Kohler et al. | |
| 5,222,963 A | 6/1993 | Brinkerhoff et al. | |
| 5,224,951 A | 7/1993 | Freitas | |
| 5,234,447 A | 8/1993 | Kaster et al. | |
| 5,250,058 A | 10/1993 | Miller et al. | |
| 5,282,810 A | 2/1994 | Allen et al. | |
| 5,314,436 A | 5/1994 | Wilk | |
| 5,324,290 A | 6/1994 | Zdeblick et al. | |
| 5,340,360 A | 8/1994 | Stefanchik | |
| 5,346,115 A | 9/1994 | Perouse et al. | |
| 5,346,501 A | 9/1994 | Regula et al. | |
| 5,354,304 A | 10/1994 | Allen et al. | |
| 5,364,399 A | 11/1994 | Lowery et al. | |
| 5,366,458 A | 11/1994 | Korthoff et al. | |
| 5,366,462 A | 11/1994 | Kaster et al. | |
| 5,403,333 A | 4/1995 | Kaster et al. | |
| 5,403,338 A | 4/1995 | Milo | |
| 5,423,826 A | 6/1995 | Coates et al. | |
| 5,425,738 A | 6/1995 | Gustafson et al. | |
| 5,431,668 A | 7/1995 | Burbank, III et al. | |
| 5,437,684 A | 8/1995 | Calabrese et al. | |
| 5,443,198 A | 8/1995 | Viola et al. | |
| 5,452,733 A | 9/1995 | Sterman et al. | |
| 5,454,824 A | 10/1995 | Fontayne et al. | |
| 5,474,732 A | 12/1995 | Korthoff et al. | |
| 5,485,947 A | 1/1996 | Olson et al. | |
| 5,486,187 A | 1/1996 | Schenck | |
| 5,488,958 A | 2/1996 | Topel et al. | |
| 5,501,698 A | 3/1996 | Roth et al. | |
| 5,503,617 A | 4/1996 | Jako | |
| 5,503,635 A | 4/1996 | Sauer et al. | |
| D372,310 S | 7/1996 | Hartnett | |
| 5,549,612 A | 8/1996 | Yapp et al. | |
| 5,643,305 A | 7/1997 | Al-Tameem | |
| 5,649,937 A | 7/1997 | Bito et al. | |
| 5,658,300 A | 8/1997 | Bito et al. | |
| 5,669,918 A | 9/1997 | Balazs et al. | |
| 5,693,064 A | 12/1997 | Arnold | |
| 5,695,504 A | 12/1997 | Gifford, III et al. | |
| 5,697,943 A | 12/1997 | Sauer et al. | |
| 5,702,412 A | 12/1997 | Popov et al. | |
| 5,707,380 A | 1/1998 | Hinchliffe et al. | |
| 5,709,335 A | 1/1998 | Heck | |
| 5,725,537 A | 3/1998 | Green et al. | |
| 5,732,872 A | 3/1998 | Bolduc et al. | |
| 5,762,256 A | 6/1998 | Mastri et al. | |
| 5,779,718 A | 7/1998 | Green et al. | |
| 5,797,931 A | 8/1998 | Bito et al. | |
| 5,797,934 A | 8/1998 | Rygaard | |
| 5,807,277 A | 9/1998 | Swaim | |
| 5,817,113 A | 10/1998 | Gifford, III et al. | |
| 5,823,956 A | 10/1998 | Roth et al. | |
| 5,827,316 A | 10/1998 | Young et al. | |
| 5,829,447 A | 11/1998 | Stevens et al. | |
| 5,833,698 A | 11/1998 | Hinchliffe et al. | |
| 5,839,639 A | 11/1998 | Sauer et al. | |
| 5,855,614 A | 1/1999 | Stevens et al. | |
| 5,860,581 A | 1/1999 | Roberts et al. | |
| 5,881,943 A | 3/1999 | Heck et al. | |
| 5,891,160 A | 4/1999 | Williamson, IV et al. | |
| 5,893,369 A | 4/1999 | Lemole | |
| 5,904,697 A | 5/1999 | Gifford, III et al. | |
| 5,906,625 A | 5/1999 | Bito et al. | |
| 5,910,153 A | 6/1999 | Mayenberger | |
| 5,916,226 A | 6/1999 | Tozzi | |
| 5,944,730 A | 8/1999 | Nobles et al. | |
| 5,944,736 A | 8/1999 | Taylor et al. | |
| 5,947,363 A | 9/1999 | Bolduc et al. | |
| 5,951,576 A | 9/1999 | Wakabayashi | |

| | | |
|---|---|---|
| 5,954,735 A | 9/1999 | Rygaard |
| 5,957,363 A | 9/1999 | Heck |
| 5,957,879 A | 9/1999 | Roberts et al. |
| 5,961,481 A | 10/1999 | Sterman et al. |
| 5,964,782 A | 10/1999 | Lafontaine et al. |
| 5,971,973 A | 10/1999 | Peters |
| 5,972,030 A | 10/1999 | Garrison et al. |
| 5,976,159 A | 11/1999 | Bolduc et al. |
| 5,976,164 A | 11/1999 | Bencini et al. |
| 5,989,277 A | 11/1999 | Le Maire, III et al. |
| 5,989,278 A | 11/1999 | Mueller |
| 5,993,464 A | 11/1999 | Knodel |
| 5,993,468 A | 11/1999 | Rygaard |
| 6,015,416 A | 1/2000 | Stefanchik et al. |
| 6,024,748 A | 2/2000 | Manzo et al. |
| 6,030,395 A | 2/2000 | Nash et al. |
| 6,036,705 A | 3/2000 | Nash et al. |
| 6,056,762 A | 5/2000 | Nash et al. |
| 6,066,144 A | 5/2000 | Wolf et al. |
| 6,080,173 A | 6/2000 | Williamson, IV et al. |
| 6,083,234 A | 7/2000 | Nicholas et al. |
| 6,110,187 A | 8/2000 | Donlon |
| 6,131,789 A | 10/2000 | Schulze et al. |
| 6,171,319 B1 | 1/2001 | Nobles et al. |
| 6,171,321 B1 | 1/2001 | Gifford, III et al. |
| 6,176,413 B1 | 1/2001 | Heck et al. |
| 6,176,864 B1 | 1/2001 | Chapman |
| 6,176,867 B1 | 1/2001 | Wright |
| 6,179,849 B1 | 1/2001 | Yencho et al. |
| 6,183,486 B1 | 2/2001 | Snow et al. |
| 6,187,019 B1 | 2/2001 | Stefanchik et al. |
| 6,187,020 B1 | 2/2001 | Zegdi et al. |
| 6,187,022 B1 | 2/2001 | Alexander, Jr. et al. |
| 6,190,397 B1 | 2/2001 | Spence et al. |
| 6,190,590 B1 | 2/2001 | Randall et al. |
| 6,193,734 B1 | 2/2001 | Bolduc et al. |
| 6,197,042 B1 | 3/2001 | Ginn et al. |
| 6,206,913 B1 | 3/2001 | Yencho et al. |
| 6,224,603 B1 | 5/2001 | Marino |
| 6,231,506 B1 | 5/2001 | Hu et al. |
| 6,234,995 B1 | 5/2001 | Peacock, III |
| 6,241,741 B1 | 6/2001 | Duhaylongsod et al. |
| 6,241,742 B1 | 6/2001 | Spence et al. |
| 6,241,743 B1 | 6/2001 | Levin et al. |
| 6,248,117 B1 | 6/2001 | Blatter |
| 6,253,984 B1 | 7/2001 | Heck et al. |
| 6,254,615 B1 | 7/2001 | Bolduc et al. |
| 6,254,617 B1 | 7/2001 | Spence et al. |
| 6,280,460 B1 | 8/2001 | Bolduc et al. |
| 6,332,468 B1 | 12/2001 | Benetti |
| 6,338,712 B2 | 1/2002 | Spence et al. |
| 6,346,074 B1 | 2/2002 | Roth |
| 6,350,252 B2 | 2/2002 | Ray et al. |
| 6,361,543 B1 | 3/2002 | Chin et al. |
| 6,371,965 B2 | 4/2002 | Gifford, III et al. |
| 6,387,105 B1 | 5/2002 | Gifford, III et al. |
| 6,391,039 B1 | 5/2002 | Nicholas et al. |
| 6,401,721 B1 | 6/2002 | Maginot |
| 6,440,146 B2 | 8/2002 | Nicholas et al. |
| 6,443,965 B1 | 9/2002 | Gifford, III et al. |
| 6,450,390 B2 | 9/2002 | Heck et al. |
| 6,451,034 B1 | 9/2002 | Gifford, III et al. |
| 6,461,365 B2 | 10/2002 | Bolduc et al. |
| 6,471,713 B1 | 10/2002 | Vargas et al. |
| 6,494,889 B1 | 12/2002 | Fleischman et al. |
| 6,503,259 B2 | 1/2003 | Huxel et al. |
| 6,562,037 B2 | 5/2003 | Paton et al. |
| 6,682,540 B1 | 1/2004 | Sancoff et al. |
| 6,726,697 B2 | 4/2004 | Nicholas et al. |
| 6,769,594 B2 | 8/2004 | Orban, III |
| 6,818,009 B2 | 11/2004 | Hart et al. |
| 7,059,510 B2 | 6/2006 | Orban, III |
| 7,169,158 B2 * | 1/2007 | Sniffin et al. .............. 606/151 |
| 7,241,302 B2 * | 7/2007 | Sniffen et al. .............. 606/184 |
| 7,438,718 B2 * | 10/2008 | Milliman et al. ........... 606/142 |
| 2003/0171775 A1 | 9/2003 | Belson |
| 2003/0181930 A1 | 9/2003 | Milliman et al. |
| 2003/0208213 A1 | 11/2003 | Manzo |
| 2004/0078047 A1 | 4/2004 | Nicholas et al. |
| 2004/0082963 A1 | 4/2004 | Gannoe et al. |
| 2004/0092971 A1 | 5/2004 | Sniffin et al. |
| 2004/0092998 A1 | 5/2004 | Sniffin et al. |
| 2004/0199182 A1 | 10/2004 | Milliman et al. |
| 2005/0010241 A1 | 1/2005 | Milliman et al. |
| 2005/0033359 A1 | 2/2005 | Dycus |
| 2006/0111731 A1 | 5/2006 | Manzo |

FOREIGN PATENT DOCUMENTS

| | | |
|---|---|---|
| EP | 594004 A1 | 4/1994 |
| EP | 643946 A | 3/1995 |
| EP | 656191 A2 | 6/1995 |
| EP | 820725 B1 | 7/1997 |
| EP | 820724 A | 1/1998 |
| EP | 885595 A1 | 12/1998 |
| EP | 1088519 A | 4/2001 |
| FR | 1518083 | 2/1968 |
| FR | 2777446 | 10/1999 |
| GB | 935490 | 8/1963 |
| WO | WO88/01486 | 3/1988 |
| WO | WO95/15715 | 6/1995 |
| WO | WO95/17127 | 6/1995 |
| WO | WO95/35065 | 12/1995 |
| WO | WO97/40754 | 11/1997 |
| WO | WO99/11178 | 3/1999 |
| WO | WO 00/09040 | 2/2000 |
| WO | WO 00/09092 | 2/2000 |
| WO | WO 00/33745 | 6/2000 |
| WO | WO00/69343 | 11/2000 |
| WO | WO 00/69343 | 11/2000 |
| WO | WO01/52748 | 7/2001 |
| WO | WO02/32323 | 4/2002 |
| WO | WO02/32324 | 4/2002 |
| WO | WO02/058568 | 8/2002 |
| WO | WO03/101314 | 12/2003 |

OTHER PUBLICATIONS

International Search Report—EPO 98110977—Sep. 25, 1998.
International Search Report—EPO 99118064- Nov. 1, 2000.
International Search Report—EPO 00120262—Dec. 20, 2000.
International Search Report—PCT/US01/02043— Nov. 7, 2001.
International Search Report—PCT/US03/18295—Oct. 28, 2003.
Information Booklet for: LIGACLIP, Ligating Clips, Appliers & Removers for Security in Ligation, Ethicon, Inc., 1982.
Information Booklet for: Deep Surgery Advantage-Dramatic New access Plus Automatic-Feed in Vessel Ligation, Hemoclip® Automatic Ligating Clip System, Edward Weck & Company, Inc. Sep. 1996.
Information Booklet for: Auto Suture® Premium Sugliclip™ Titanium Disposable Clip Appliers, United States Surgical Corporation, 1981.

* cited by examiner

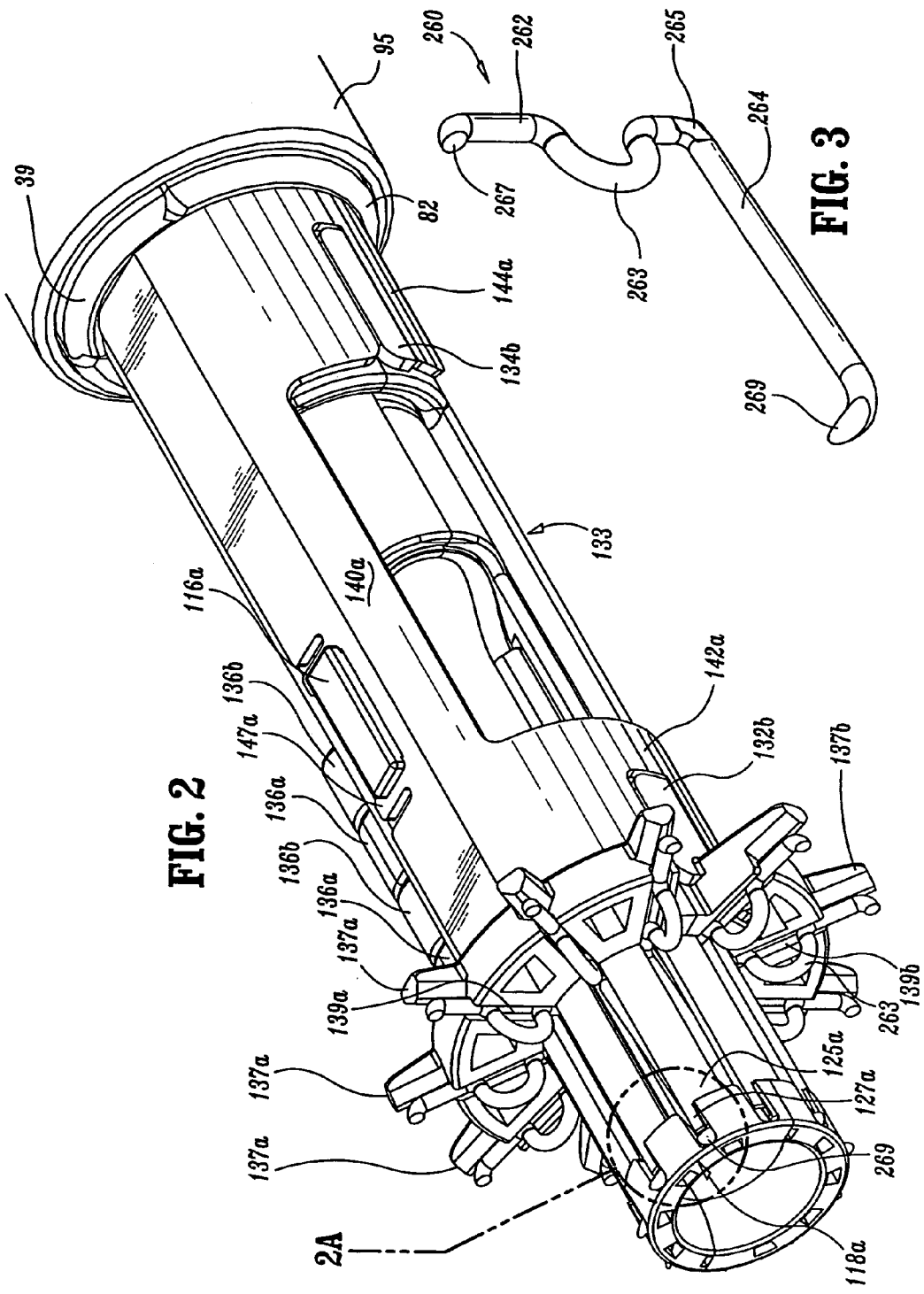

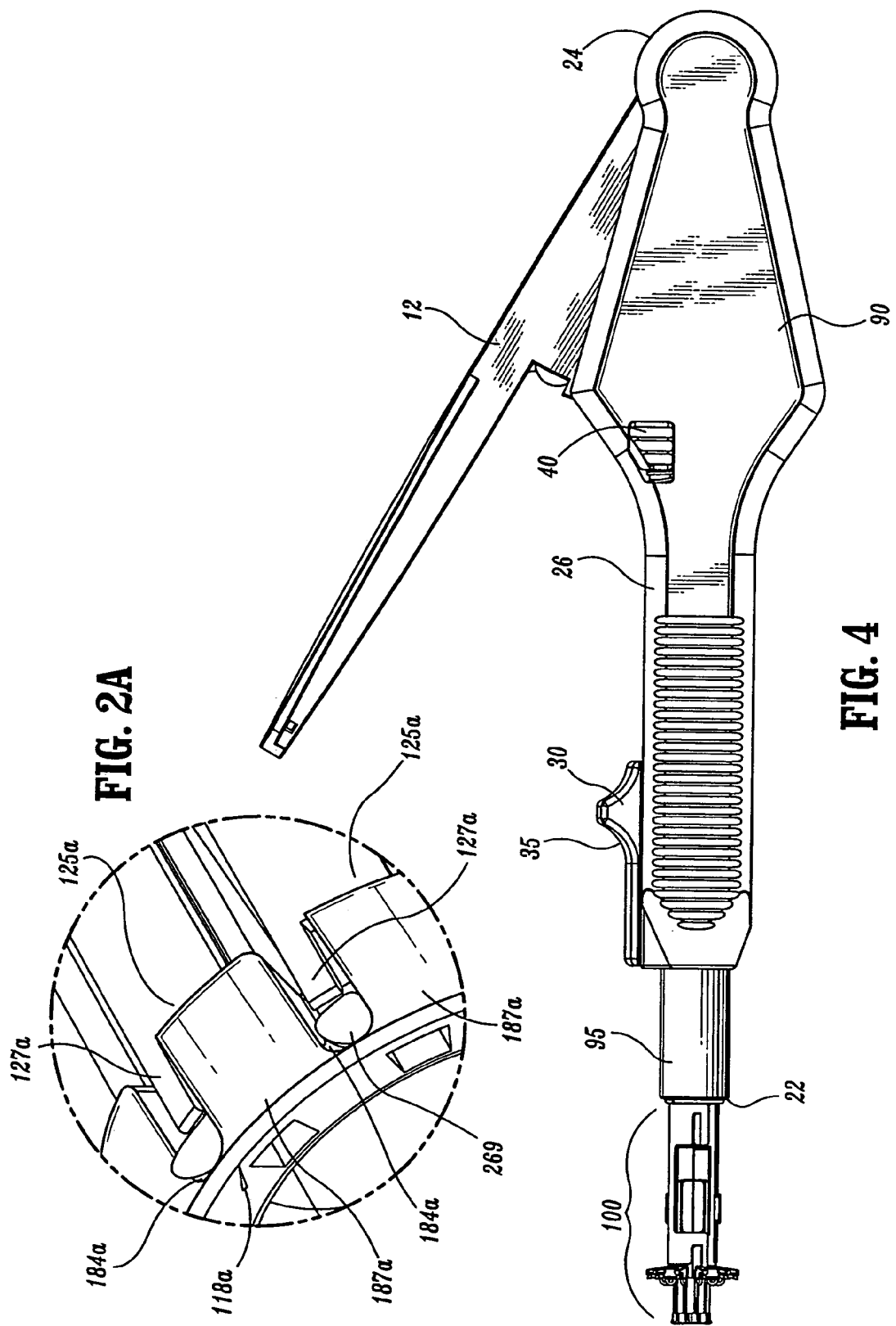

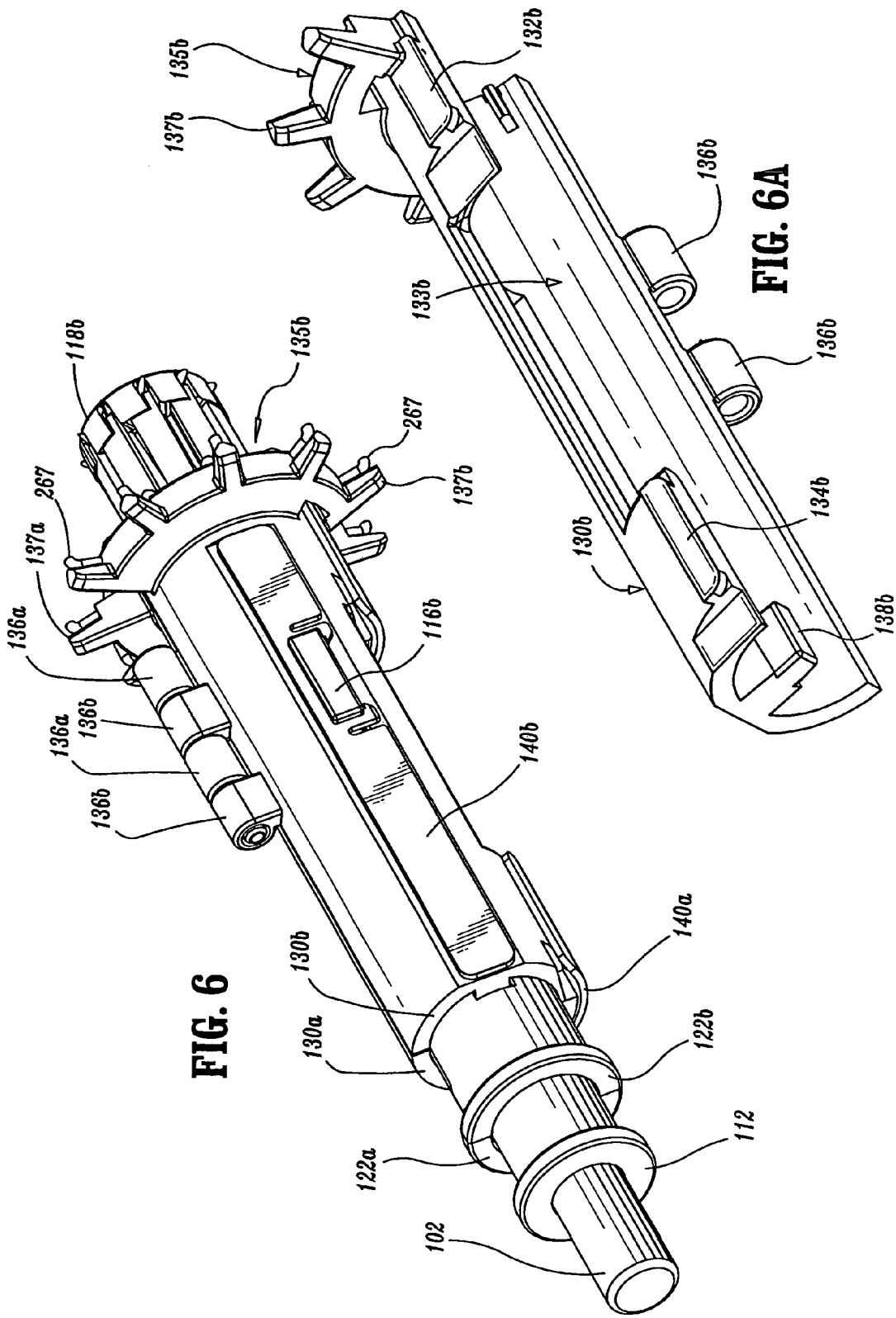

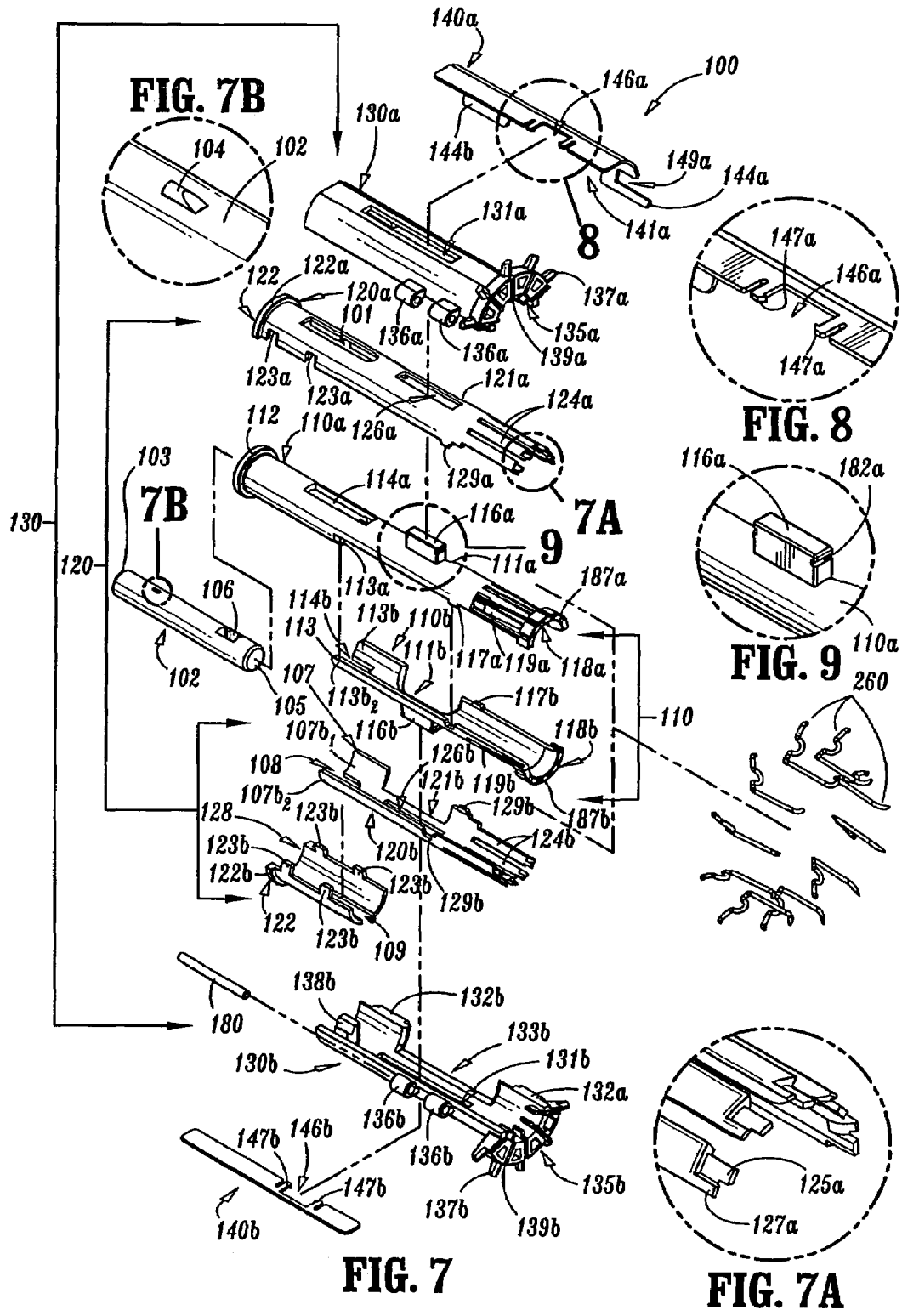

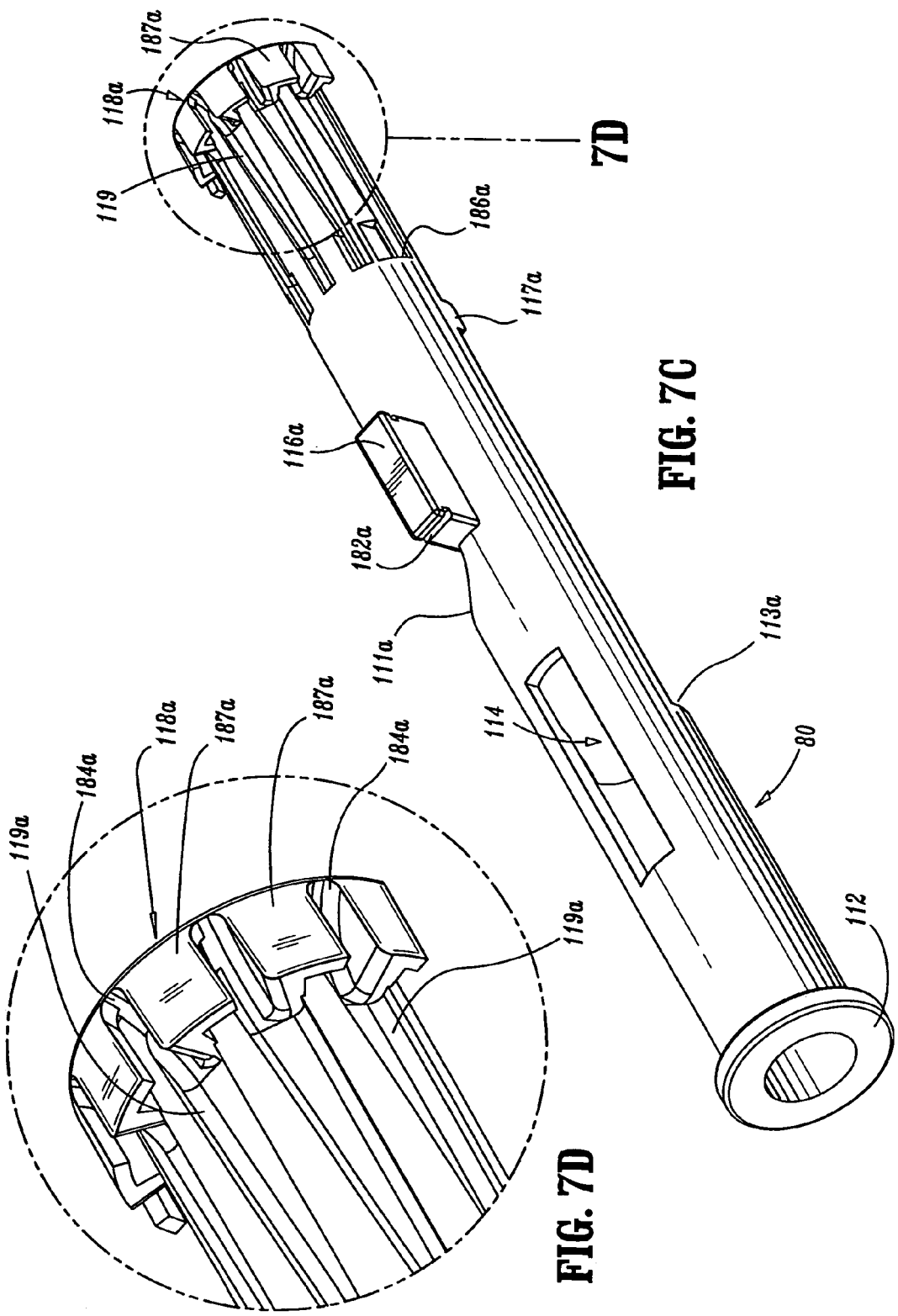

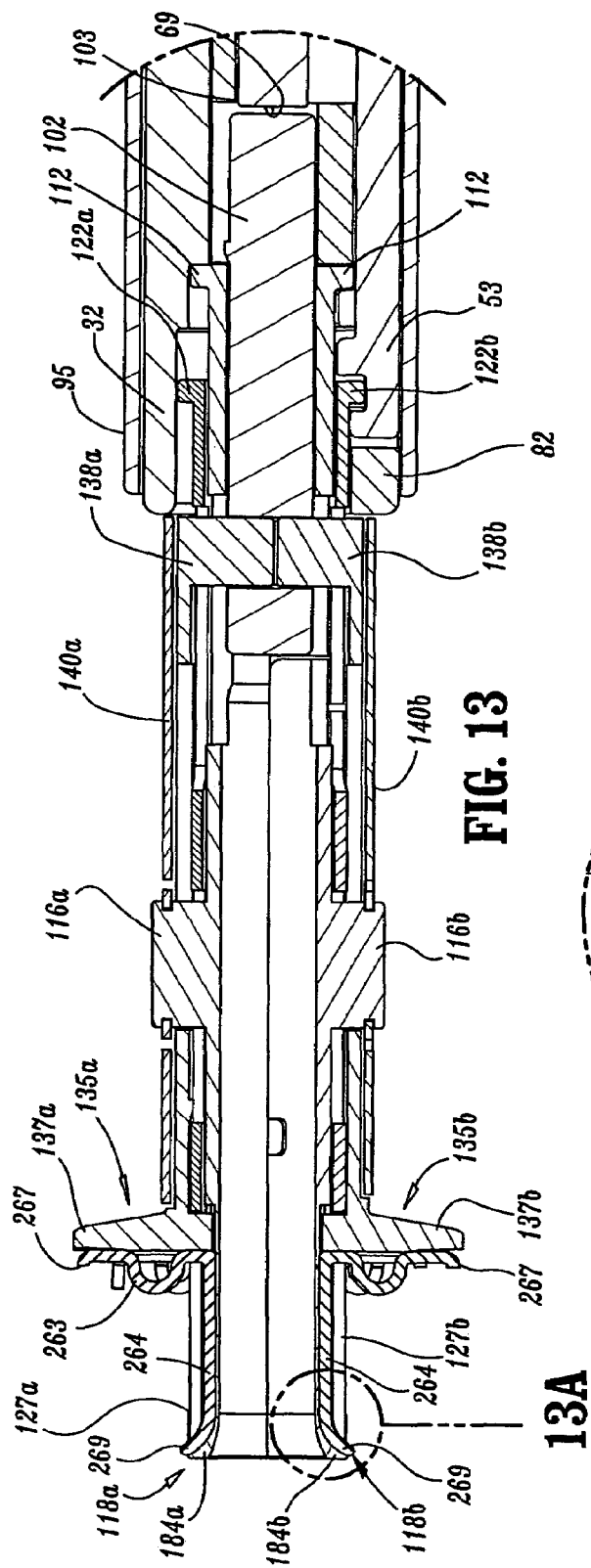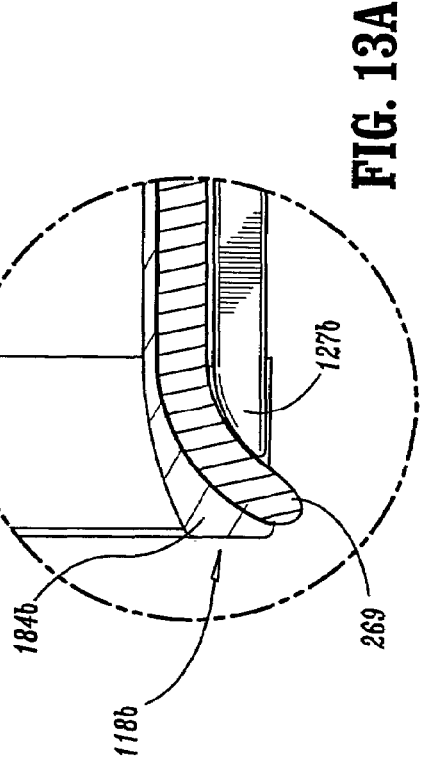
FIG. 13
FIG. 13A

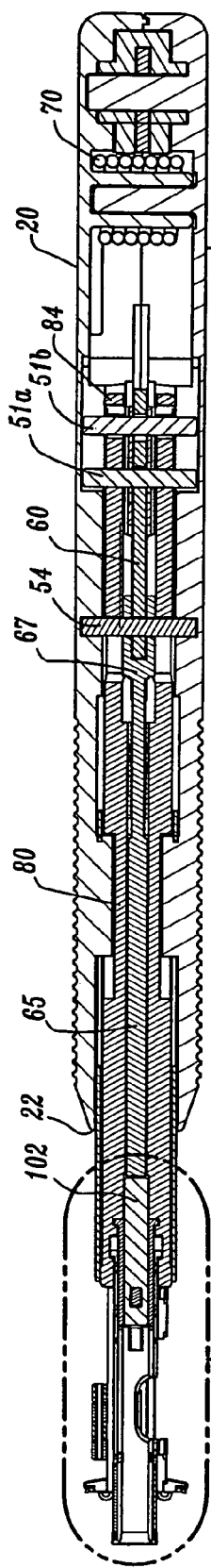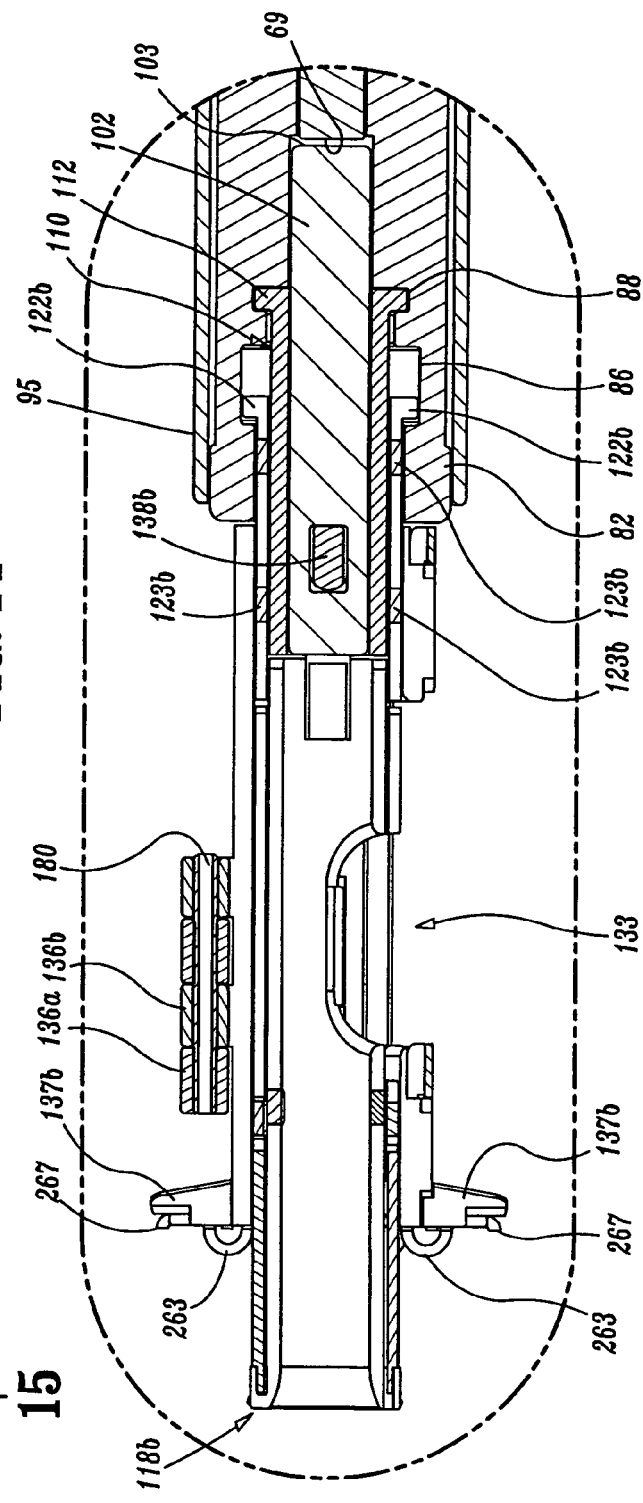
FIG. 14
FIG. 15

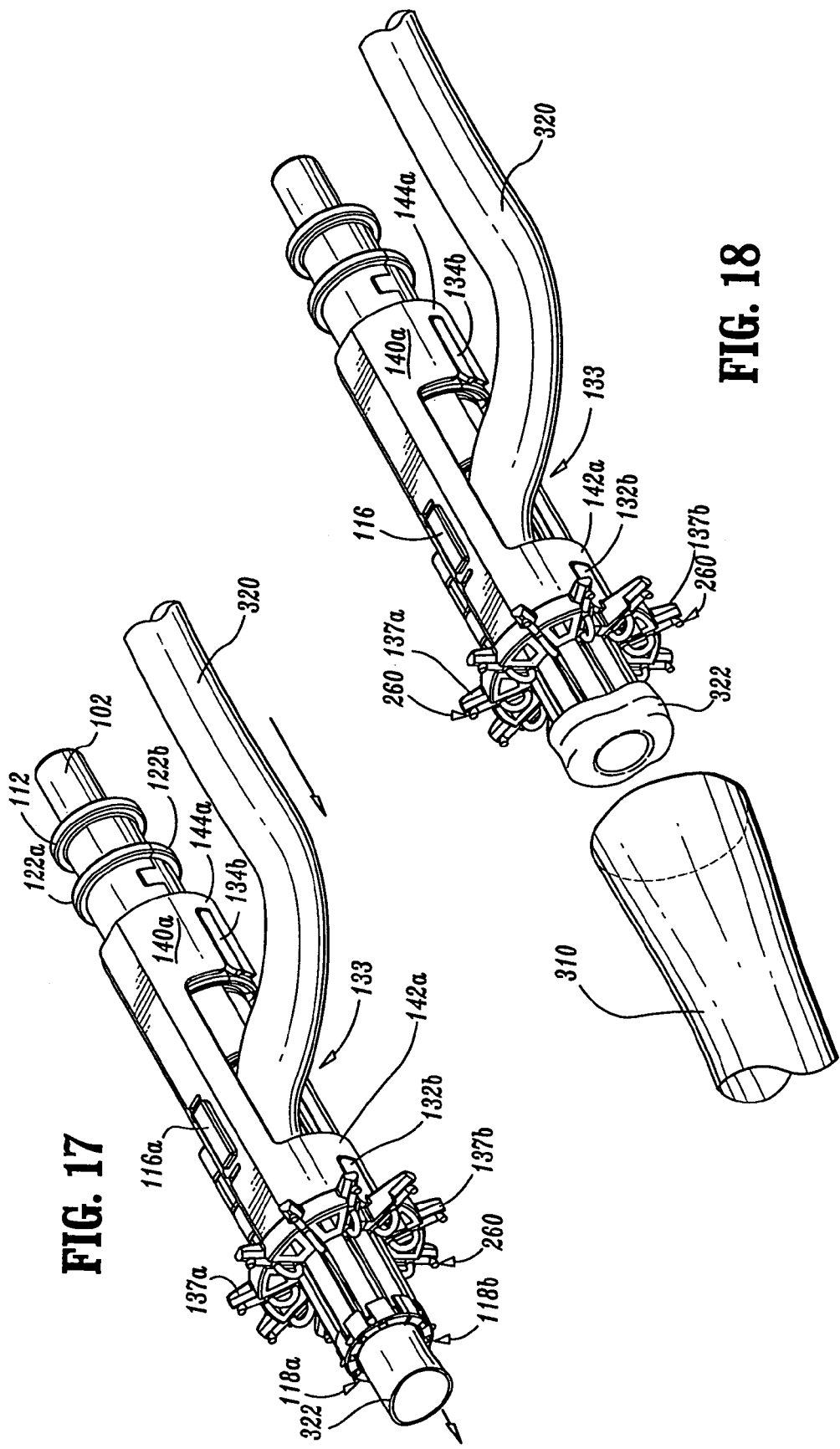

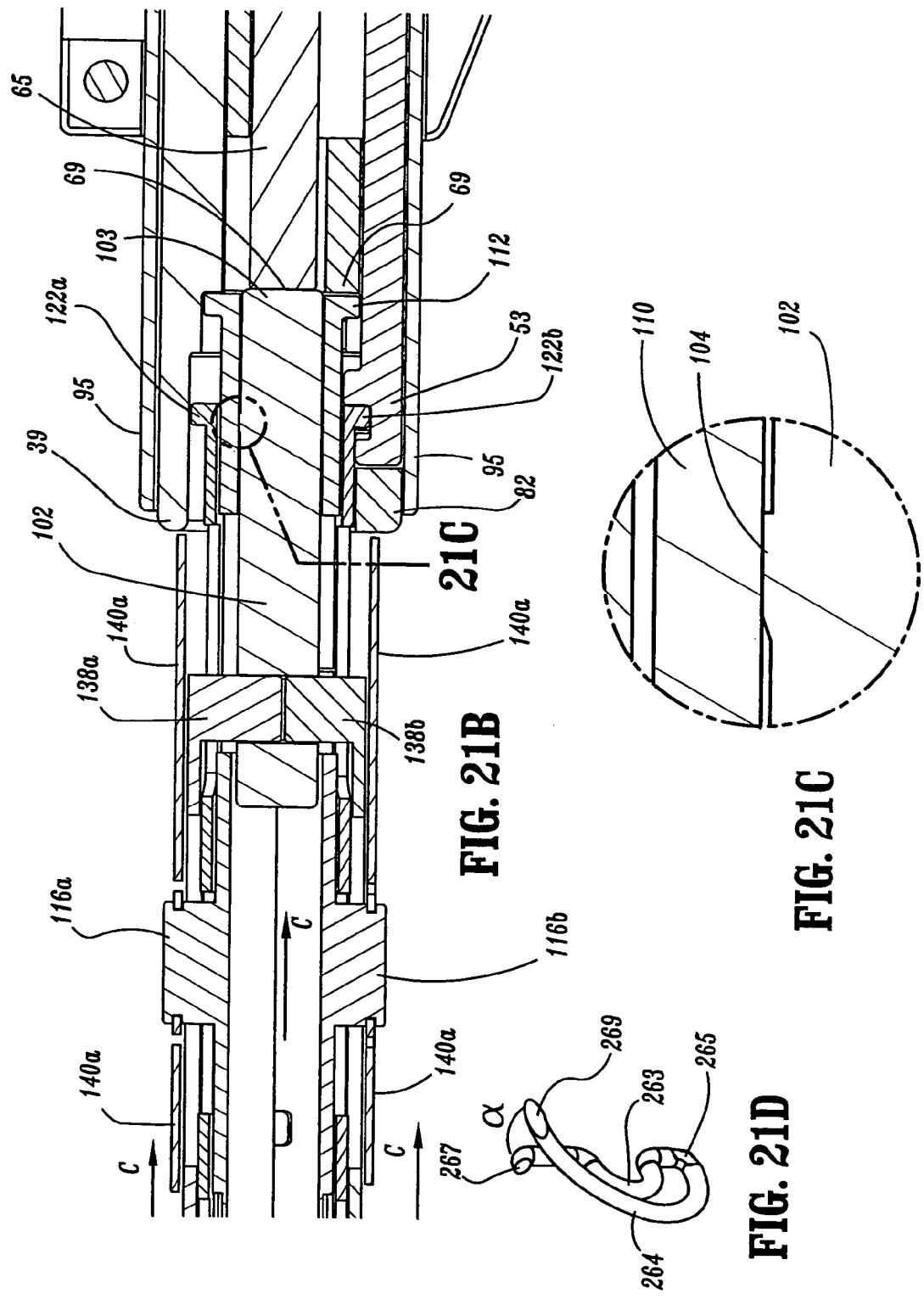

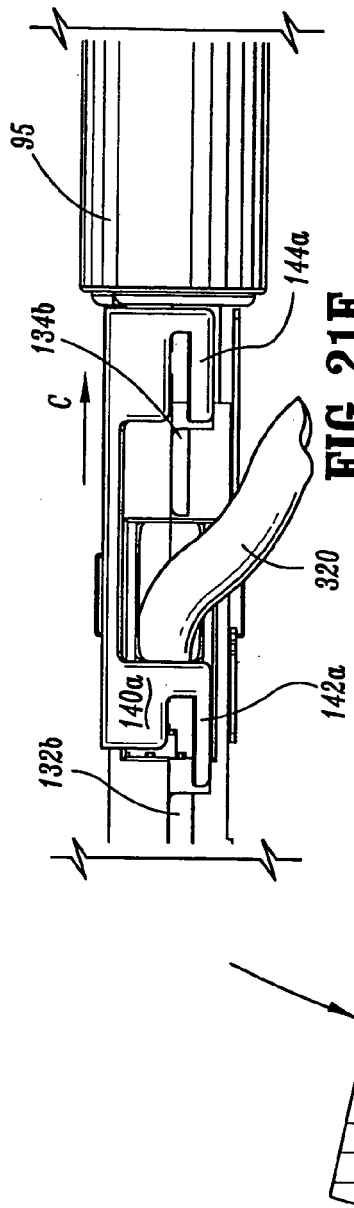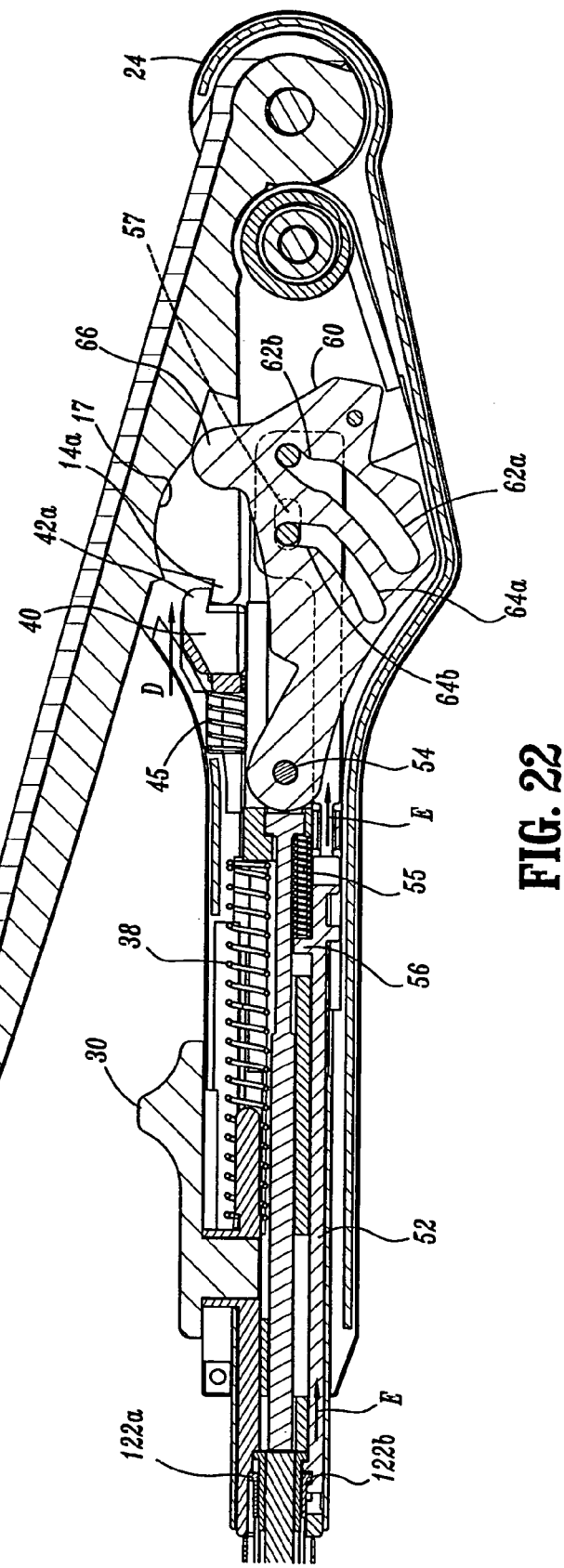

END-TO-END ANASTOMOSIS INSTRUMENT AND METHOD FOR PERFORMING SAME

CROSS REFERENCE TO RELATED APPLICATIONS

This application is a continuation of U.S. application Ser. No. 10/993,544 filed Nov. 19, 2004 entitled "END-TO-END ANASTOMOSIS INSTRUMENT AND METHOD FOR PERFORMING SAME" now U.S. Pat. No. 7,059,510 which claims the benefit of priority to PCT Application Ser. No. PCT/US03/18295 filed May 30, 2003 entitled "END-TO-END ANASTOMOSIS INSTRUMENT AND METHOD FOR PERFORMING SAME" which claims the benefit of priority to U.S. patent application Ser. No. 10/160,460 filed on May 31, 2002 entitled "END-TO-END ANASTOMOSIS INSTRUMENT AND METHOD FOR PERFORMING SAME", now U.S. Pat. No. 6,769,594, the entire contents of all of which being hereby incorporated by reference herein.

BACKGROUND

The present disclosure relates to a surgical instrument and method for performing anastomosis of tubular body structures, and more particularly to an instrument for joining tubular tissues, for example, during gastrointestinal procedures.

Surgical stapling devices for applying an annular array of staples or fasteners to tissue are well known in the art. For example, surgical stapling devices for applying an annular array of staples, as well as devices for completing a surgical anastomosis through the provision of anastomosis rings, are well known in gastric and esophageal surgery, for example in classic or modified gastric reconstruction typically formed in an end to end, end to side, or side to side manner.

These devices generally include a circular array of fasteners such as staples, anastomosis rings, and the like, while the anvil member includes means for completing the circular anastomosis, typically an array of bucket members that cinch the staples after the staples are expelled from the fastener assembly, or may include a locking member for the anastomosis ring.

In use, the anvil is positioned within the lumen of an organ such as the stomach, esophagus, or intestine and the tissue is pulled about and around the anvil member and tied off, e.g., by a purse string suture, ring mechanism or the like. The fastener assembly is then positioned within the opposite end of the lumen and the tissue is pulled about and around the fastener assembly over the staple array and also tied off. At this point the tissue is positioned between the anvil and the fastener assembly. The anvil is typically slowly retracted (or advanced) to approximate the two tissue halves prior to deformation of the staples usually by virtue of a wing-nut and worm gear assembly which allows a surgeon to methodically advance the anvil towards the staple array to hold the tissue between the anvil and the fastener assembly. Many prior art devices also provide a visual indicator to signal the surgeon when the anvil has reached a firing position adjacent the staple or fastener assembly.

The surgeon then unlocks a safety device deform the staples against the anvil. As the staples or the fasteners are expelled from the fastener assembly, a circular knife typically follows the application of the staples to excise unwanted tissue at the anastomosis site. The instrument is then removed from the lumen of the organ.

The closing mechanisms associated with the prior art stapling or fastening devices typically utilize a complex worm gear arrangement or screw bearing member to approximate the spacing between the anvil and the fastener assembly. As mentioned above, this requires additional manipulation of the instrument by the surgeon during the surgery, e.g., the surgeon must grasp the device with one hand while rotating the knob or wing-like assembly with the other hand. As can be appreciated, moving the anvil member the full distance towards the fastener assembly can be a time consuming process during the surgical procedure. For example, many of the known prior art devices require 15 to 20 full 360° rotations of the knob or wing nut assembly to fully close the instrument in order to fire or expel the staples or fasteners into the tissue.

As can be appreciated, it would be advantageous to eliminate many of the above steps for performing the circular anastomosis of these tissue structures to expedite the overall surgical procedure. It would also be extremely advantageous to simplify the overall anastomosis procedure and reduce the level of manual intervention by the surgeon with respect to tying off the tubular ends prior to staple deformation. Moreover, it would be advantageous to provide an instrument which can perform end-to-end anastomosis deep within a tubular structure, e.g., colon, where known prior art devices cannot reach and the surgeon is forced to perform an gastrotomy and then make an incision within the side of the tubular structure to utilize these prior art devices.

A need also exists to develop a device which can be useful for low anterior resection of the colon which has proven difficult with a number of prior art devices. In addition, it would be useful to provide a device where the eversion of the tissue is exterior to the colon which facilitates future repair if needed and reduces the chances of stenosis at the anastomosis site. It would also be helpful to provide an instrument which reduces the amount of healthy tissue removed from the site during the anastomosis.

SUMMARY

The present disclosure relates to a surgical instrument for performing an end-to-end anastomosis of first and second luminal structures, such as two portions of the small intestine during a gastrointestinal procedure. The instrument includes a housing having an actuator attached thereto and a selectively removable loading unit attached to a distal end of the housing. The loading unit is dimensioned to support an array of surgical fasteners at a distal end thereof. Upon activation of the actuator, the surgical fasteners simultaneously deform against a moveable anvil such that a distal end of each of the surgical fasteners secures each end of each luminal structure to complete the end-to-end anastomosis. As can be appreciated, simultaneous deformation of the surgical fasteners against the movable anvil is advantageous since it greatly reduces overall operating time compared to manual suturing and also provides uniformity across the anastomosis site which tends to reduce leakage.

In one embodiment, the surgical fasteners include a convexity and a base leg which cooperate after deformation of the surgical fasteners to securely retain the two luminal structures in close abutment with one another. Preferably, the distal ends of the surgical fasteners penetrate at least one of the ends of one of the luminal structures. In another embodiment, the surgical fasteners include a base leg and a proximal portion and the surgical fasteners are supported in the loading unit in an angular manner relative to a longitudinal axis extending through the loading unit. Upon deformation, the base legs of the surgical fasteners deform at an angle relative to the proximal portions of the surgical fasteners. As can be appreciated, deformation of the surgical fasteners in a radially offset manner allows the surgical fasteners to more fully deform and essentially "pinch" the two adjoining tissues in closer abutment against one another which tends to further enhance the anastomosis and reduce leakage.

In yet another embodiment according to the present disclosure, the loading unit is disposable and includes two halves which are pivotable relative to one another. Preferably, the two halves of the loading unit when closed form an elongated aperture for receiving the first luminal structure therethrough. Prior to activation of the actuator, the two halves of the loading unit are pivotally secured relative to one another. Upon actuation, the two halves are unsecured allowing the halves to pivot relative to one another to release the first luminal structure from within the elongated aperture. As can be appreciated, automatically releasing the first luminal structure from the loading unit after deformation is advantageous in the operating theatre since it reduces operating time and manual handling of the luminal structure after the anastomosis which may unintentionally compromise the overall integrity of the end-to-end anastomosis.

In still yet another embodiment, the distal end of the loading unit includes an anvil for retaining the distal ends of the surgical fasteners and for supporting an everted end of the first luminal structure. Preferably, the anvil includes an angled surface which causes the distal ends of the surgical fasteners to deform proximally during firing. As mentioned above, this is particularly advantageous because it allows the surgical fasteners to more fully deform and compress or pinch the tissue into tight abutting relationship with one another to enhance the anastomosis.

In another embodiment, the loading unit includes a series of elongated channels each having a distal end and a proximal end. Each distal end of each channel is radially offset from each proximal end such that the proximal and distal ends of the surgical fasteners are supported in a radially offset manner within the loading unit.

The surgical fasteners are deformable upon activation of the actuator such that a distal end of each surgical fastener secures each end of each luminal structure to complete the end-to-end anastomosis wherein the resulting eversion is exterior to the luminal structures. As can be appreciated, making the eversion exterior to the luminal structures is advantageous since it reduces the chances of fibrin stenosis and/or infection at the anastomosis site.

In another embodiment of the present disclosure, the handle includes a locking flange which locks the handle in an actuated configuration. Preferably, the locking flange is bifurcated and cooperates with a release tab to allow the user to selectively release the selectively disposable loading unit. The housing advantageously includes a thumb tab which is movable from a first position for receiving the selectively disposable loading unit to a second position for securing the selectively disposable loading unit. As can be appreciated, these features are advantageous since they tend to greatly simplify the overall operation of the surgical instrument and provide the surgeon with certain lockout controls and safety mechanisms during and after the firing processes.

In yet another embodiment, the actuator includes at least one cam member. Preferably, the cam member includes two cam followers which ride along two cam slots defined within the cam member. Advantageously, each cam follower mechanically engages first and second retracting sleeves, respectively, such that movement of the cam follower moves a respective retracting sleeve.

Preferably, one of the cam slots includes two cam stages, a first stage for retracting a first retracting sleeve for deformation of the surgical fasteners and a second stage for retracting the first retracting sleeve relative to the second retracting sleeve. Advantageously, movement of the first retracting sleeve in the second stage unsecures the halves of the selectively disposable loading unit to allow the halves to pivot relative to one another to release the first luminal structure from within the aperture. As can be appreciated and as mentioned above, this reduces unnecessary handling of the luminal structures after the anastomosis.

The present invention also relates to a method for creating an end-to-end anastomosis between first and second luminal structures. The method includes the steps of: providing a surgical instrument which includes: a housing having an actuator; a disposable loading unit removably mounted to the housing, the disposable loading unit being configured to releasably support a plurality of surgical fasteners; and a retractable anvil being movable to simultaneously deform the surgical fasteners. The method also includes the steps of: inserting an end of the first luminal structure into a passage defined within the loading unit; everting the first luminal structure over the retractable anvil; inserting a distal end of the disposable loading unit into an end of the second luminal structure such that a distal end of each of the plurality of fasteners and the first luminal structure are sufficiently inserted into the second luminal structure and the intimae of the two luminal structures abut one another; and activating the actuator to retract the anvil to simultaneously deform the surgical fasteners and, preferably, to cause distal and/or proximal ends of a plurality of surgical fasteners to penetrate the luminal structures and complete the end-to-end anastomosis wherein the resulting eversion is exterior to the luminal structures.

BRIEF DESCRIPTION OF THE DRAWINGS

Other objects and features of the present invention will become apparent from the following detailed description considered in connection with the accompanied drawings. It should be understood, however, that the drawings are designed for the purpose of illustration only and not as a definition of the limits of the invention.

An illustrative embodiment of the subject surgical instrument and method are described herein with reference to the drawings wherein:

FIG. 2 is an enlarged, partial perspective view of a single use loading unit (hereinafter "SULU") constructed in accordance with a preferred embodiment of the present disclosure;

FIG. 2A is an enlarged, perspective view of the indicated area of detail of FIG. 2;

FIG. 3 is a perspective view of a surgical fastener which is designed for operative engagement with the SULU for creating an end-to-end anastomosis between two luminal vessels;

FIG. 4 is a side view the surgical instrument of FIG. 1;

FIG. 6 is a reverse, perspective view of the SULU of FIG. 2;

FIG. 6A is a reverse, perspective view of a lower half of the SULU of FIG. 2;

FIG. 7 is a perspective view with parts separated of the SULU of FIG. 2;

FIG. 7A is a greatly enlarged, perspective view of the indicated area of detail of FIG. 7;

FIG. 7B is a greatly enlarged, perspective view of the indicated area of detail of FIG. 7;

FIG. 7C is an enlarged, perspective view of a base portion of a first retracting sleeve;

FIG. 7D is a greatly enlarged, perspective view of the indicated area of detail of FIG. 7C;

FIG. 8 is a greatly enlarged, perspective view of the indicated area of detail of FIG. 7;

FIG. 9 is a greatly enlarged, perspective view of the indicated area of detail of FIG. 7;

FIG. 13 is a horizontal cross-sectional view of the indicated area of detail of FIG. 12;

FIG. 13A is a greatly enlarged horizontal cross sectional view of the area indicated in detail of FIG. 13;

FIG. 14 is a top cross-sectional view of the surgical instrument taken along section line 14-14 of FIG. 12;

FIG. 15 is a greatly enlarged top cross-sectional view of the area indicated in detail of FIG. 14;

FIG. 17 is a perspective view of the SULU with a first luminal structure inserted therethrough;

FIG. 18 is perspective of the SULU with an end of the first luminal structure everted over a distal end of the disposable unit being inserted into a second luminal structure;

FIG. 21B is a side cross-sectional view showing the movement of the SULU during the first firing stage to deform the surgical fasteners;

FIG. 21C is a greatly enlarged side cross-sectional view of the area indicated in detail in FIG. 21B;

FIG. 21D is a greatly enlarged perspective view of the surgical fastener shown in a "stapled" configuration;

FIG. 21E is a side view showing the relevant movement of a locking sleeve after the first firing stage;

FIG. 22 is a side cross-sectional view of the actuator assembly during the second firing stage and showing the internal movement of a second retractor within the actuator assembly;

DETAILED DESCRIPTION

Figure 1:
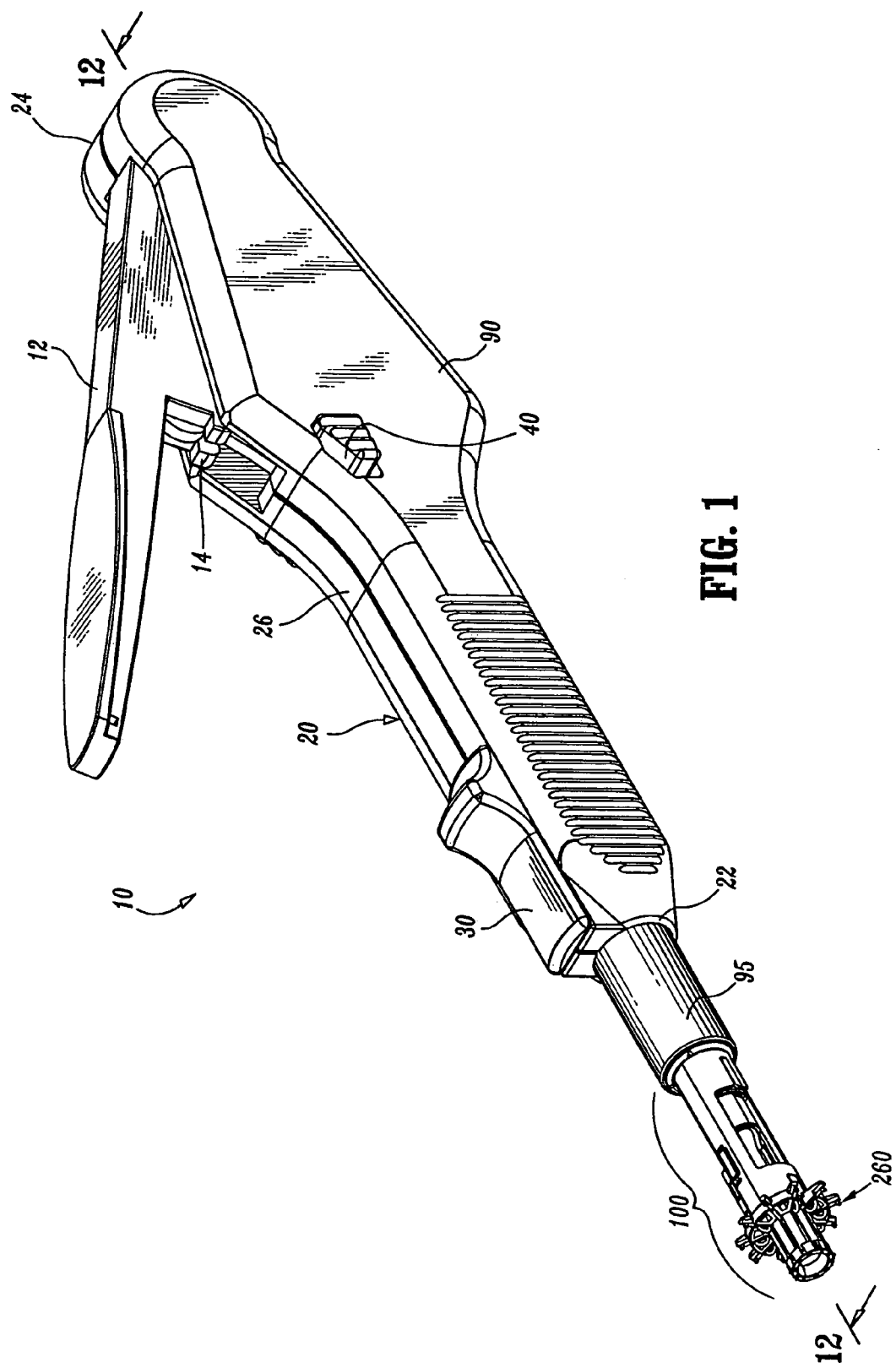
FIG. 1 is a perspective view of a surgical instrument constructed in accordance with an embodiment of the present disclosure.
Figure 4A:
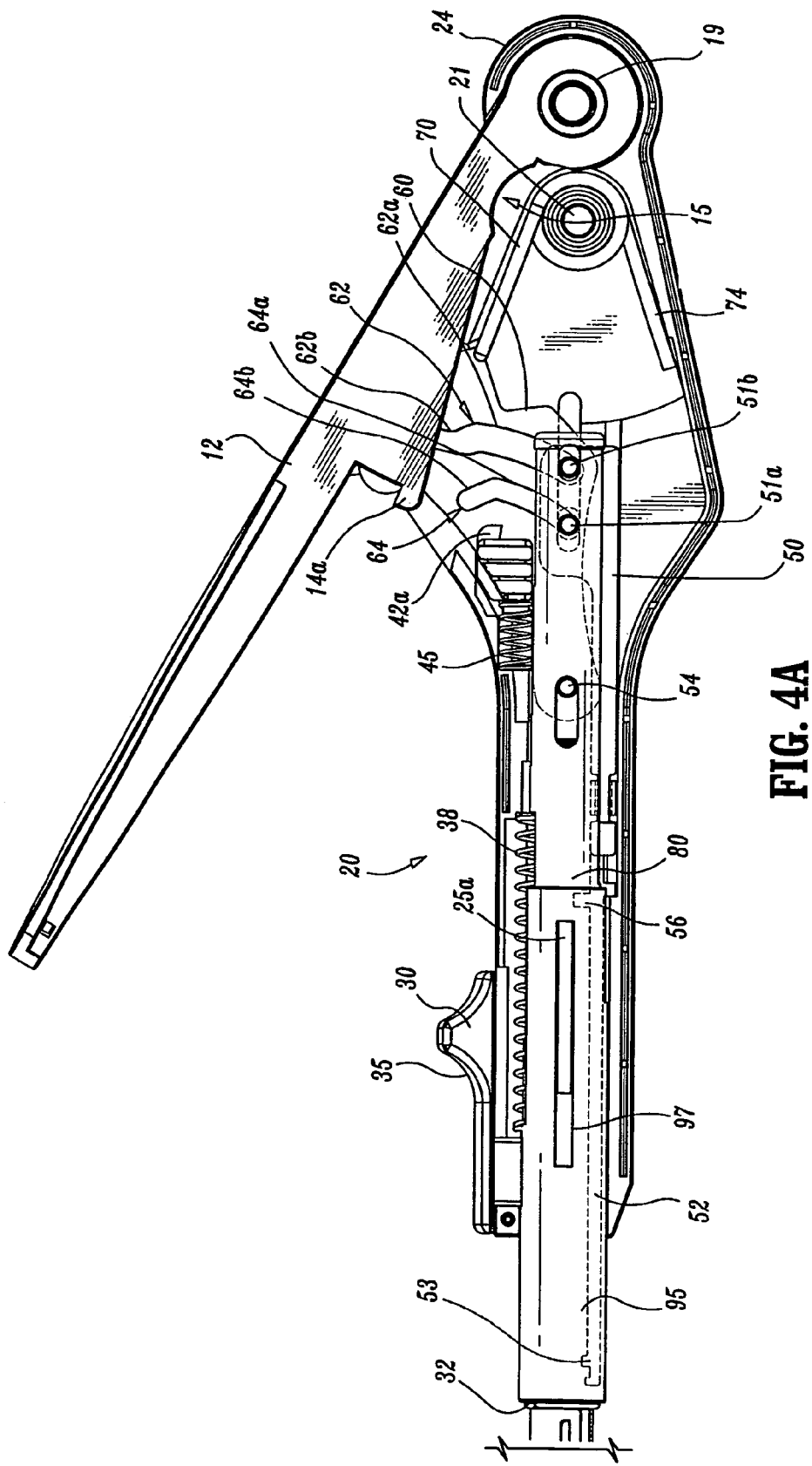
FIG. 4A is a left, side view of a handle/actuator assembly of the surgical instrument of FIG. 1 shown without a cover plate attached thereto.

Various embodiments of the surgical instrument and method disclosed herein will be described in terms of a gastrointestinal procedure wherein an end-to-end circular anastomosis is created by joining two sections of a two luminal structures, e.g., the colon and/or the small intestine. Alternatively, the presently disclosed surgical instrument may also be utilized in performing end-to-end anastomosis of other tubular luminal body structures for other surgical procedures.

In the drawings and in the description which follows, the term "proximal", as is traditional, will refer to the end of the apparatus which is closer to the user, while the term "distal" will refer to the end which is further from the user.

Referring now in detail to the drawing figures in which like reference numerals identify similar or identical elements, one embodiment of the present disclosure is illustrated generally in FIG. 1 and is designated therein as surgical instrument 10. Surgical instrument 10 includes two principal components, namely, an actuator assembly 20 and a disposable loading unit ("DLU") or a single use loading unit ("SULU") 100, which along with their internal working components, mechanically cooperate to deform a surgical fastener 260 to complete an anastomosis between luminal structures.

The particular surgical instrument 10 shown in the various figures is preferably designed to deform an array of surgical fasteners similar to fastener 260 shown in FIG. 3 which is generally L-shaped and includes a base leg 264 and an upwardly extending support leg 262. Preferably, base leg 264 includes a distal end 269 which is sufficiently shaped to penetrate a first luminal structure 320 upon deformation of the surgical fastener 260. The upwardly extending support leg 262 is attached to base leg 264 at a pivot point 265 and includes an inwardly extending prong 267 disposed at its free end designed to surgical fastener 260 in position after the completed anastomosis. It is envisioned that pivot point 265 may also be dimensioned to include a relief or coined section (not shown) which facilitates formation of the surgical fastener 260.

Turning back in detail to FIG. 3, a convexity 263 projects inwardly between the base leg 264 and the support leg 262 and is preferably sufficiently dimensioned to cooperate with the base leg 264 to retain the first luminal structure 320 against the second luminal structure 310 in fluid communication after anastomosis as will be explained in greater detail below with respect to FIGS. 21B, 24A and 24D. It is envisioned that the surgical fastener 260 can be arranged on the SULU in different patterns/arrays depending upon a particular purpose or to achieve a particular result.

As best seen in FIGS. 1, 4, 10 and 11, actuator assembly 20 includes a proximal end 24, a distal end 22 and a housing 26 defined therebetween for storing the internal working components of the actuator assembly 20. Preferably, a plate 90 covers the internal components of the actuator assembly 20 when assembled. More particularly, housing 26 includes at least one mechanical interface 23a which reciprocates with a corresponding mechanical interface 23b (FIG. 10) disposed on cover plate 90 to matingly engage the two components 26 and 90.

Actuator assembly 20 also includes a handle 12 which initiates firing of the surgical instrument 10 and a spring-loaded thumb tab 30 for loading the SULU 100 onto the actuator assembly 20 both of which will be explained in greater detail below. Preferably, handle 12 is provided with an ergonomic surface which is contoured and configured to be comfortably gripped by the hand of the user during operation of the instrument.

Figure 11:
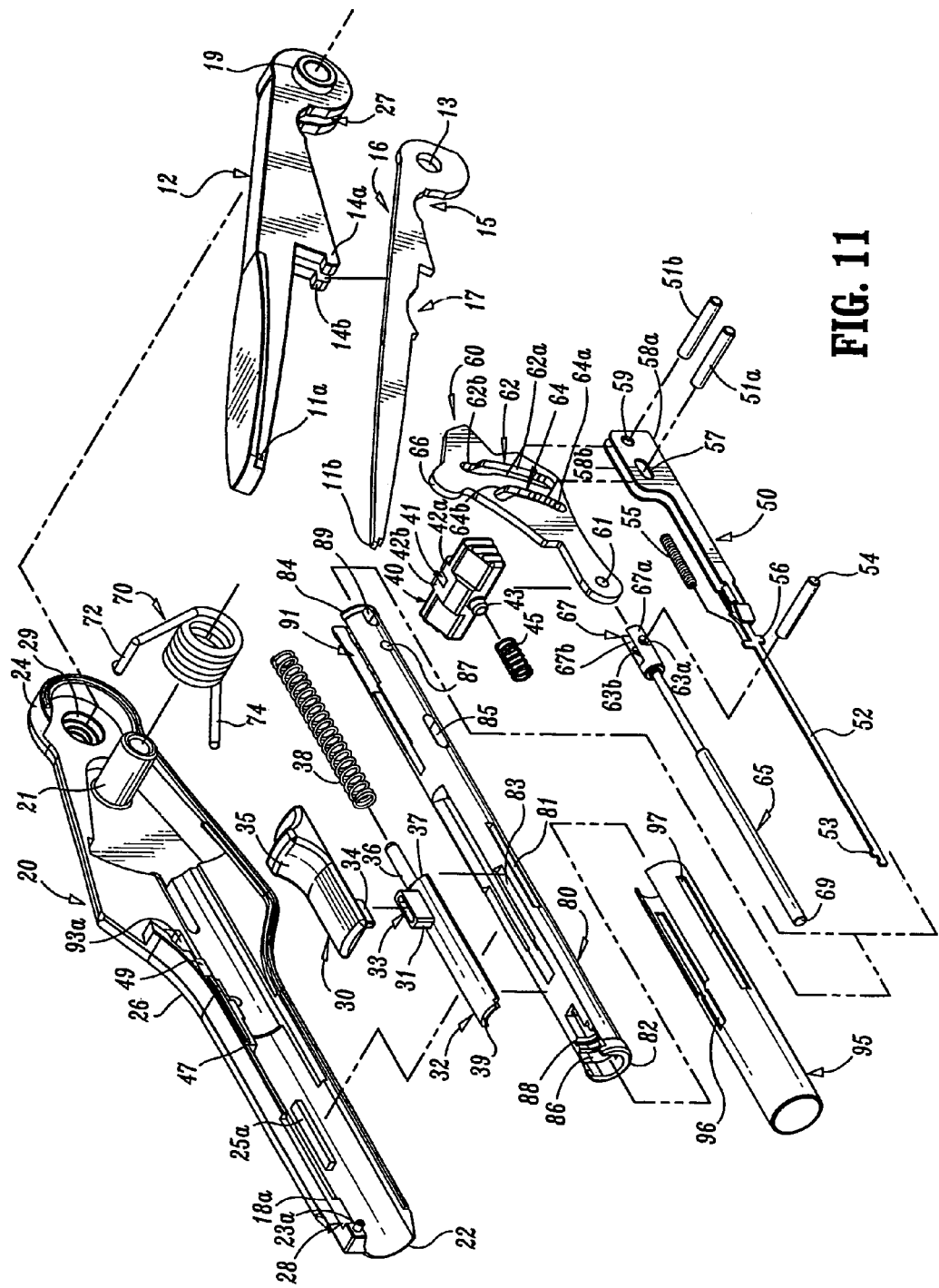
FIG. 11 is a perspective view the actuator assembly of FIG. 10 shown with parts separated.

Turning briefly to FIG. 11 which illustrates in detail the internal working components of the actuating assembly 20 which are preferably assembled and stored within housing 26. More particularly, the actuating assembly 20 includes a torsion spring 70 which mounts about post 21 which protrudes from housing 26. Spring 70 includes a lower arm 74 which is biased against a lower portion of the housing and an upper arm 72 which is biased against a rotating two-stage cam 60.

Handle 12 includes a bushing 19 which protrudes laterally from the proximal end of the handle 12 and pivotally engages a corresponding recess 29 disposed within the proximal end 24 of housing 26 to allow pivotal movement of the handle 12 with respect to housing 26. Handle 12 also includes a vertically extending slot 27 disposed at its proximal end 24 which receives the proximal end of a lever 16 which moves in conjunction with the handle 12. A pair of flanges 14a and 14b downwardly extend from the handle 12 and receive lever 16 therebetween. A mechanical interface 11a disposed on handle 12 engages a corresponding mechanical interface 11b disposed on lever 16 to secure the lever 16 to the handle 12. Preferably, lever 16 has a first recess 17 shaped to engage and control the movement of the cam 60 during downward movement of the handle 12, the purpose of which will be explained in more detail with respect to FIG. 21A. Lever 16 also includes a second recess 15 which helps to limit lateral movement of the torsion spring 70 within housing 26.

Figure 10:
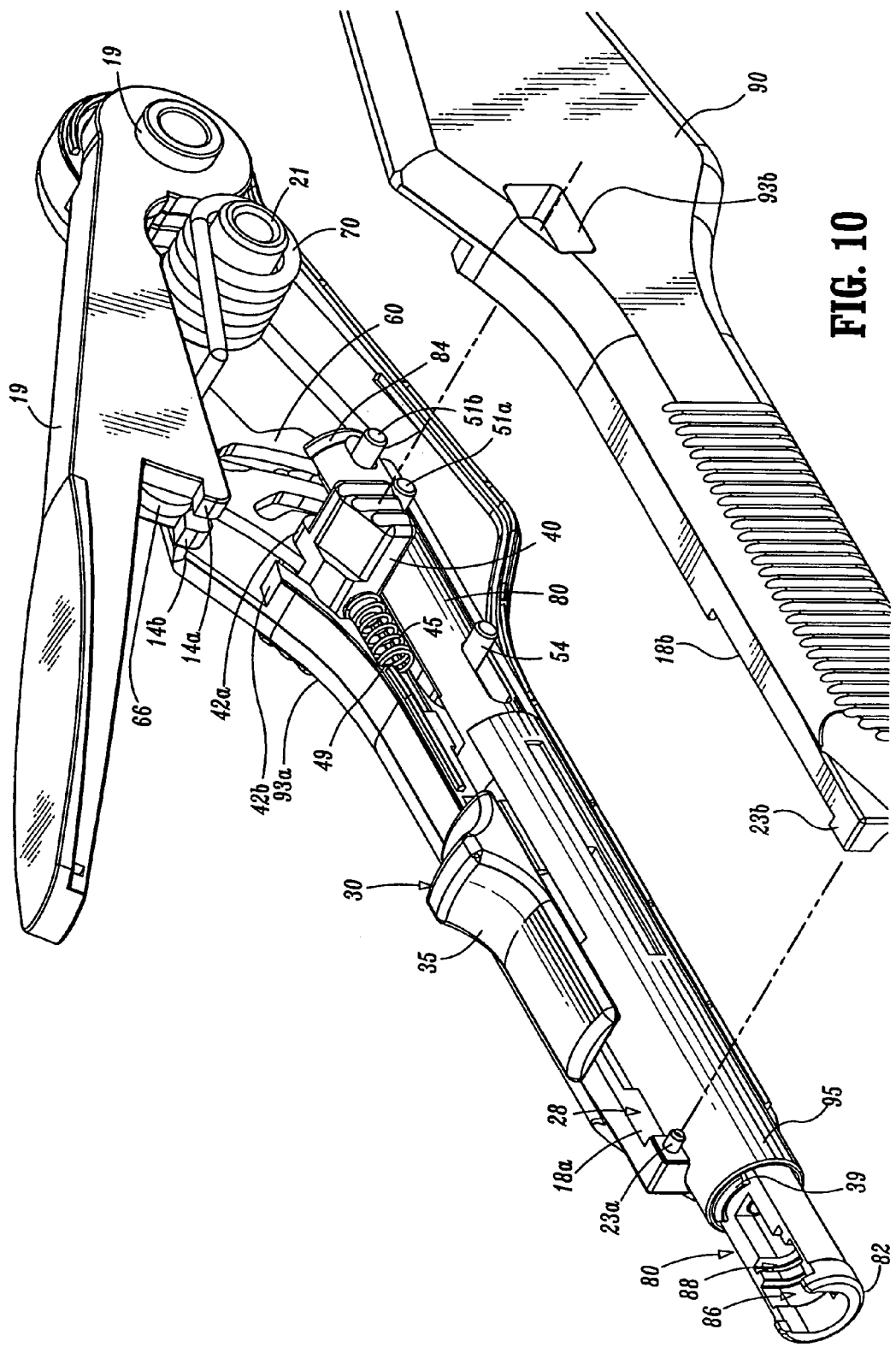
FIG. 10 is a perspective view of the actuator assembly with the cover plate shown separated.

As mentioned above, actuating assembly 20 also includes a spring-loaded thumb tab 30 which rests atop housing 26 within a longitudinally extending slot 28 disposed near the distal end 22 thereof. As best seen in FIG. 10, slot 28 is formed by notches 18a and 18b of the housing 26 and cover plate 90, respectively. Tab 30 includes a thumb guide 35 which cooperates with a sliding sleeve 32 to facilitate proximal movement of the tab 30 for loading the SULU. A downwardly depending flange 34 disposed on tab 30 engages a corresponding slot 33 located in a mount 31 disposed atop the sliding sleeve 32. Preferably, sliding sleeve 32 includes a post 36 which is dimensioned to receive a tension spring 38 thereon. Spring 38 is biased between a block 47 disposed within housing 26 and a proximal edge 37 of sliding sleeve 32 such that spring 38 biases sliding sleeve 32 to a distal-most position proximate distal end 22. Preferably, a distal end 39 of sleeve 32 is arcuate or semi-circular and is dimensioned to slidingly engage a corresponding end 82 of a first retractor 80 to lock the SULU 100 within the actuator assembly 20 after the SULU 100 is loaded as will be discussed in more detail below.

Actuator assembly 20 also includes first retractor 80 and a second retractor 50 which each move by way of movement of the handle 12 which, in turn, imparts movement to the two-stage cam 60. First retractor 80 includes distal and proximal ends 82 and 84, respectively, and is generally tubular in dimension with the exception of an elongated furrow 83 extending proximally from distal end 82 for slidingly supporting sleeve 32. Retractor 80 also includes a slot 85 for receiving a pin 54 for affixing the retractor 80 to the cam 60 and another pair of slots 87 and 89 located near the proximal end 84 for receiving two cam followers 51a and 51b, respectively. Preferably, the proximal end 84 is bifurcated to facilitate insertion of the second retractor 50 therein.

Figure 16:
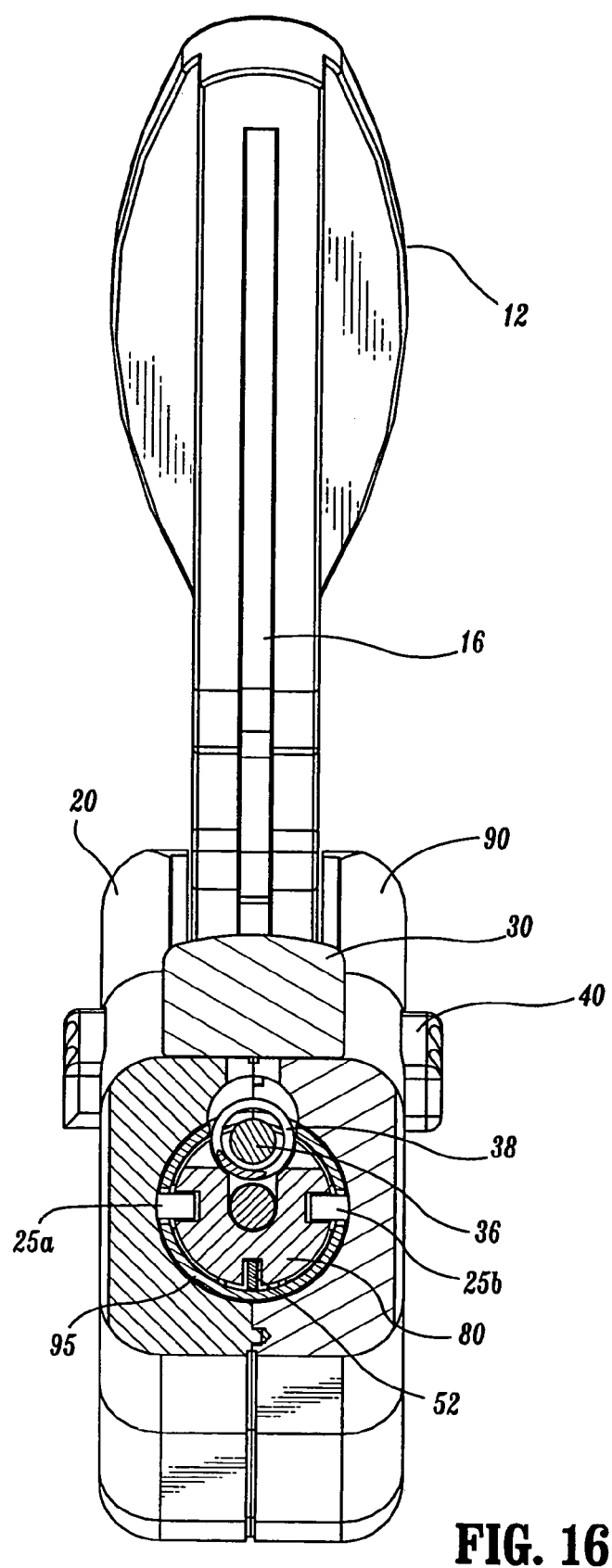
FIG. 16 is a front cross-sectional view of the surgical instrument taken along section line 16-16 of FIG. 12.
Figure 19A:
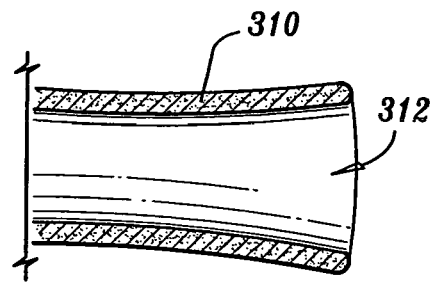
FIG. 19A is enlarged, cross-sectional view of the second luminal structure.
Figure 19B:
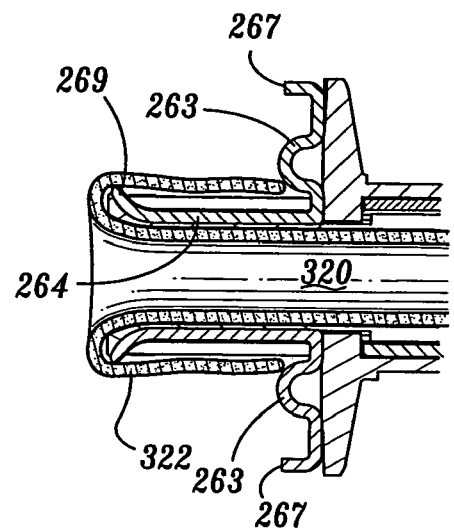
FIG. 19B is enlarged, cross-sectional view of the first luminal structure shown everted atop the distal end of the SULU.

As best seen in FIGS. 11 and 16, a guide 81 engages an elongated rib 25a in housing 26 and an elongated rib 25b in cover plate 90 to slidingly mount the retractor 80 to housing 26. Guide 81 is dimensioned slightly longer than rib 25a to permit proximal movement of the first retractor 80 relative to the housing 26 upon activation of the handle 12. Preferably, a protective tube 95 is telescopically disposed about the first retractor 80 and moves in conjunction with the sliding sleeve 32 by way of slot 96 which secures mount 31 of the sliding sleeve 32 therein. It is anticipated that protective tube 95 also helps to restrict lateral movement of the first retractor 80 during retraction. Tube 95 also includes an elongated channel 97 which generally aligns with guide 81 located in the first retractor 80 to mount both components to ribs 25a and 25b.

Figure 5:
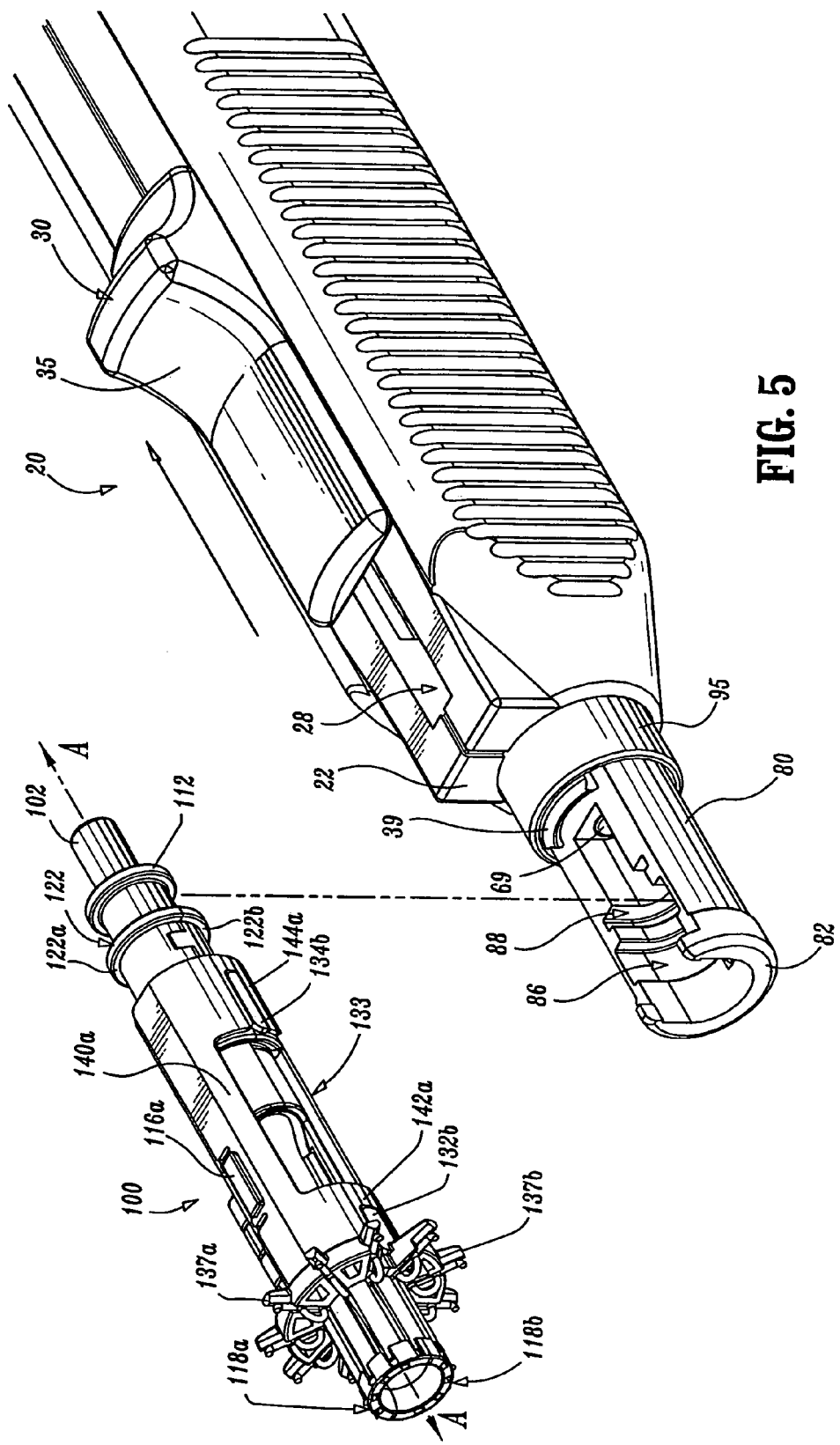
FIG. 5 is an enlarged, perspective view of a distal end of the actuator assembly shown in a pre-loading position to receivingly engage the SULU.

It is contemplated that proximal movement of tab 30 will impart reciprocating proximal movement to the sliding sleeve 32 to expose carriages 86 and 88 disposed within the first retractor 80 which are designed to receive a pair of first and second retracting sleeves 110 and 120 (FIGS. 7-9) of the SULU 100. More particularly, and as best seen in FIG. 5, carriage 86 is generally circular in shape and is designed to receive an outer lip 122 formed by the union of end 122a and 122b of second retracting sleeve 120 of the SULU 100. Preferably, carriage 86 is dimensioned larger that the lip 122 so as to permit proximal movement of the second retracting sleeve 120 relative to the first retracting sleeve 110 as will be explained in more detail with respect to FIG. 22A. Carriage 88 is likewise circular in shape and receives outer lip 112 of the first retracting sleeve 110.

Figure 12:
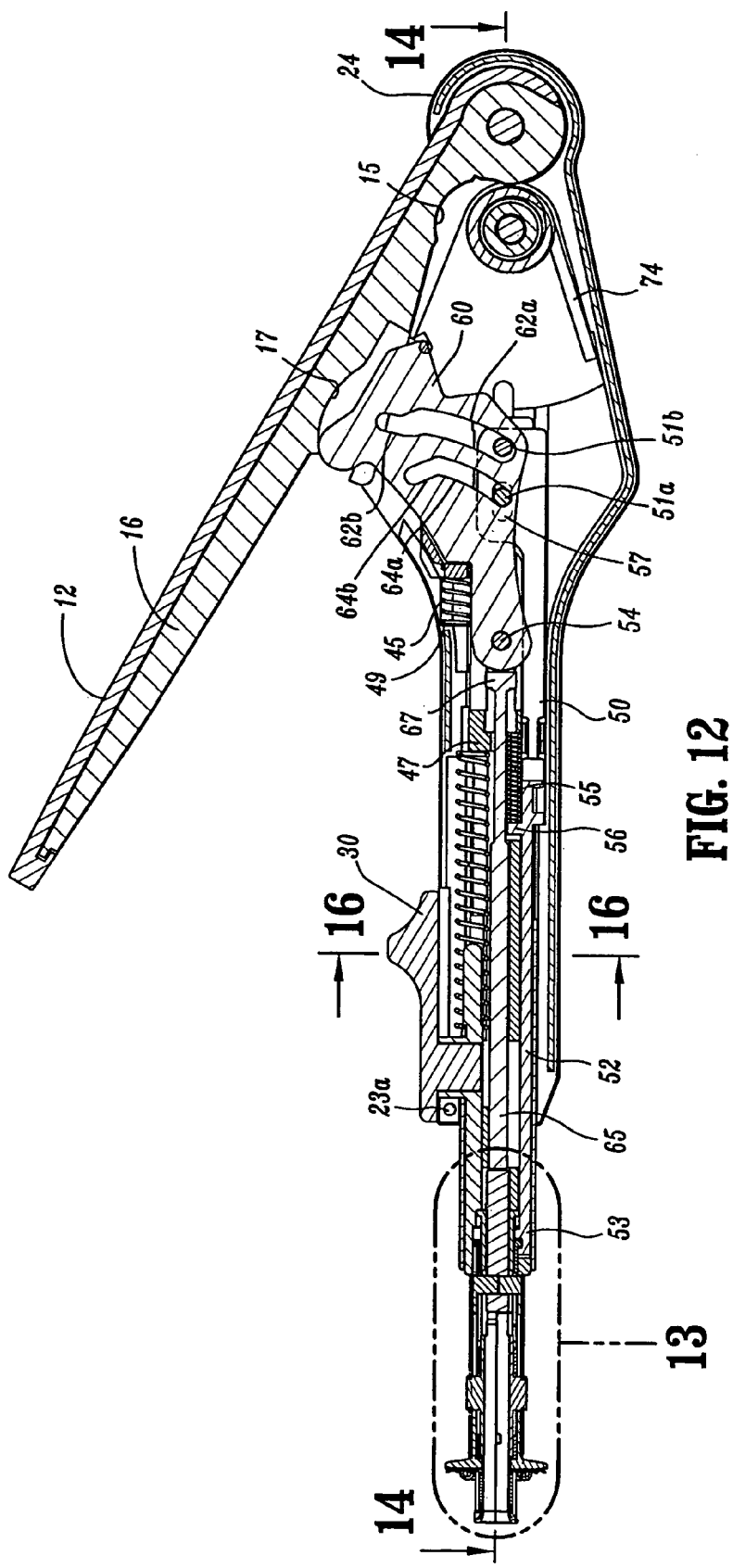
FIG. 12 is a horizontal cross-sectional view of the surgical instrument of FIG. 1 shown preloaded for firing.
Figure 21:
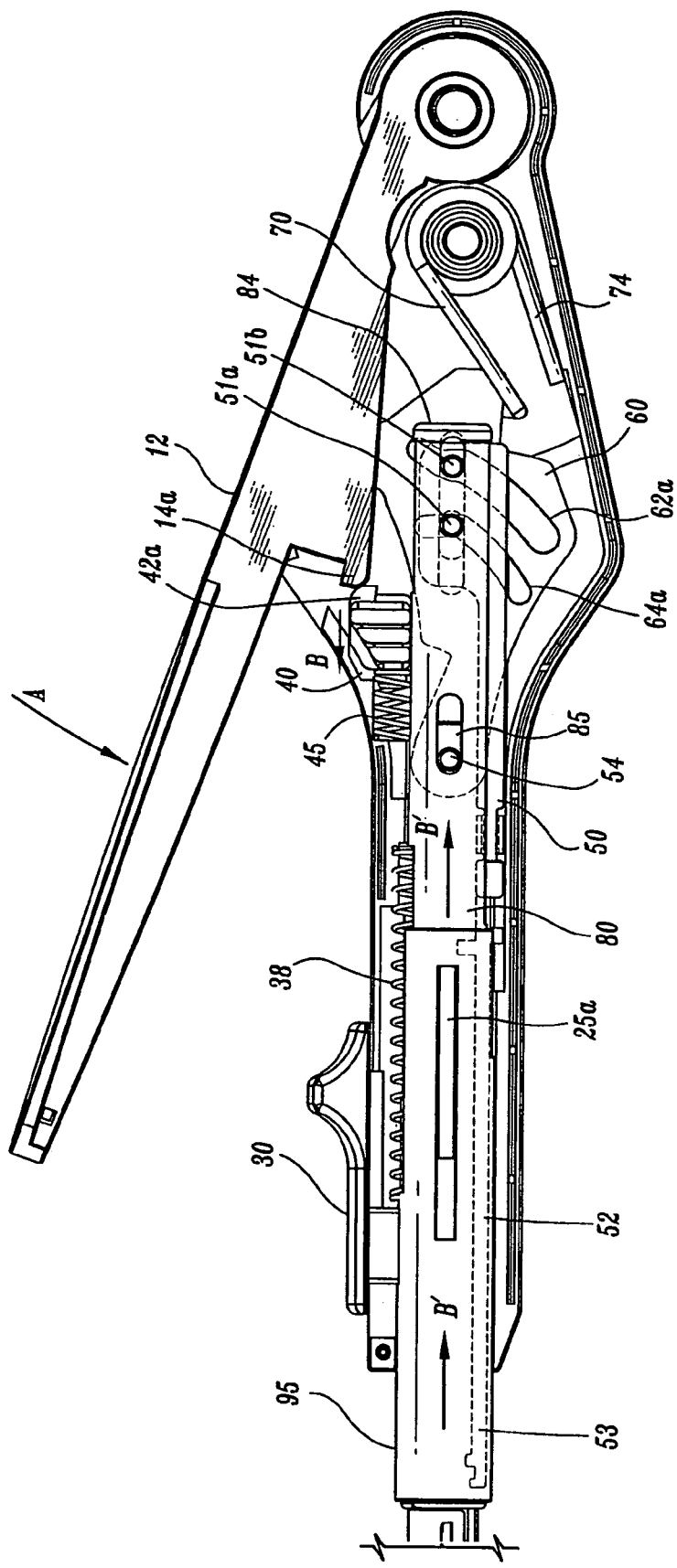
FIG. 21 is a side view of the actuator assembly without the cover plate during a first firing stage of the instrument and showing the internal movement of a first retractor within the actuator assembly.

Actuator assembly 20 also includes a handle lock 40 which rests atop the first retractor 80 and extends laterally between the housing 26 and the cover plate 90. More particularly, handle lock 40 is mounted within slots 93a and 93b as best seen in FIG. 10. Handle lock 40 includes a post 43 which receives a spring 45 for biasing handle lock 40 against a ledge 49 of the housing 26 (FIG. 12). Handle lock 40 also includes a pair of flanges 42a and 42b which align with flanges 14a and 14b disposed on handle 12. As shown best in FIGS. 21 and 22, downward movement of the handle 12 forces the handle lock 40 initially distally against spring 45 until flanges 14a and 14b clear flanges 42a and 42b at which point spring 45 forces handle lock 40 proximally to lock flanges 42a and 42b atop flanges 14a and 14b and to lock handle 12 in a downwardly disposed position. Preferably, flanges 42a and 42b define a slot 41 for receiving lever 16 therebetween.

Actuator assembly 20 also includes a second retractor 50 which includes an elongated arm 52 having a key-like distal end 53 and a T-shaped heel section 56. Preferably, T-shaped heel section 56 attaches to a tension spring 55 disposed proximally thereof. Second retractor 50 is preferably bifurcated at its proximal end forming two longitudinally extending fins 58a and 58b each having a slot 57 and aperture 59 for receiving cam followers 51 and 51b, respectively. It is contemplated that spring 55 is biased against an elongated stop 65 which rests atop arm 52 and biases heel section 56 proximally when the second retractor 50 is retracted which will be explained in more detail below with respect to the operation of the surgical instrument 10.

As mentioned above, the first retractor 80 is affixed to two-stage cam 60 by pin 54. More particularly, cam 60 includes an aperture 61 located near the distal end thereof for receiving pin 54 which affixes the cam 60 to the first retractor 80. Cam 60 also includes a pair of generally vertical arcuately-shaped slots 62 and 64 which each include two discrete stages, namely 62a, 62b and 64a, 64b, respectively, for imparting movement to corresponding followers 51a and 51b. A nub 66 is located near the uppermost portion of the cam 60 and is dimensioned to slideably engage recess 17 located in lever 16 as best illustrated in FIG. 12.

Figure 21A:
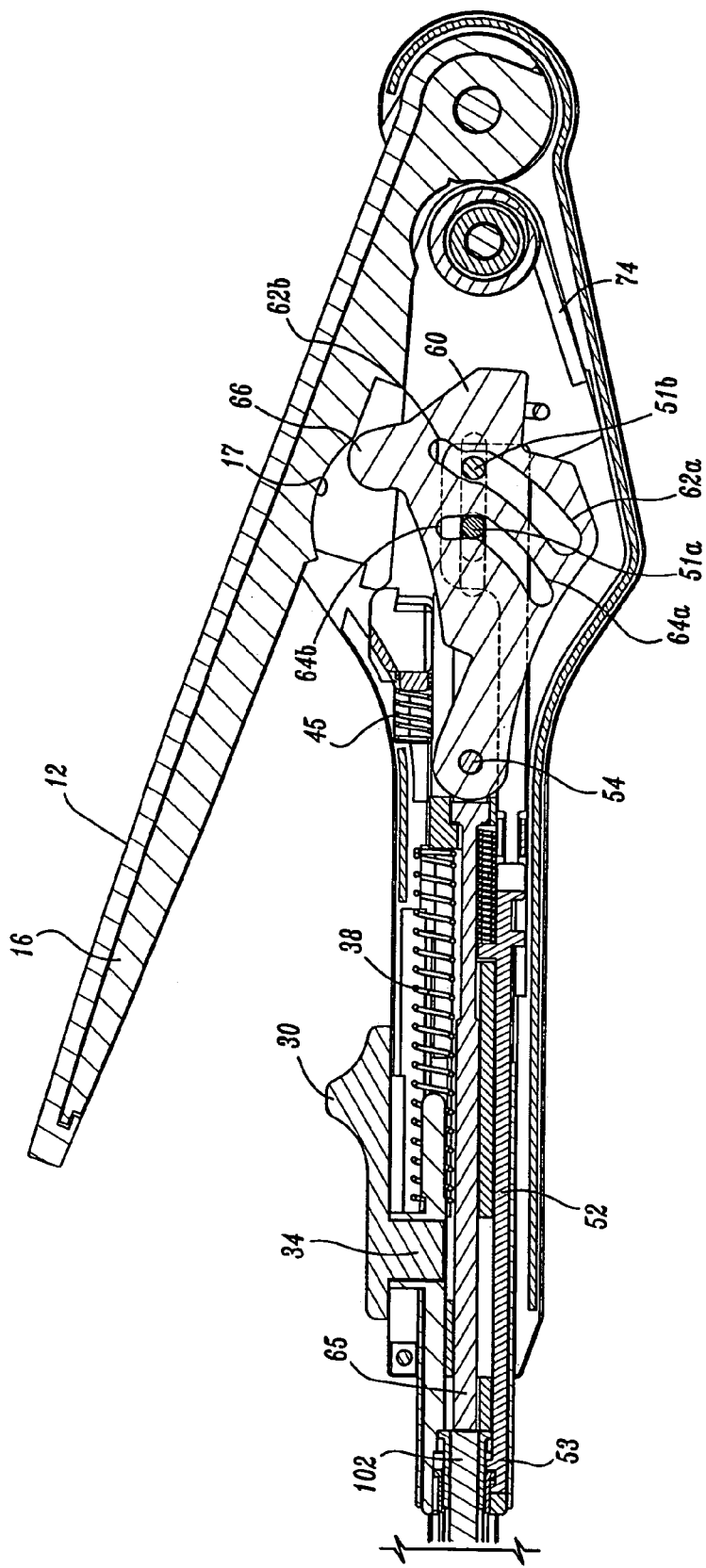
FIG. 21A is a side cross-sectional view showing the relevant positions of the internal working components of the actuator assembly after the first firing stage.

It is contemplated that during downward movement of handle 12, lever 16 will bias nub 66 downwardly such that nub 66 rides proximally along recess 17 and causes cam 60 to pivot downwardly about pin 54 as shown best in FIGS. 21A and 22. In turn, followers 51a and 51b will ride along slots 64 and 62 and cause the first and second retractors 80 and 50 to move in a proximal direction which will be explained in more detail below. Preferably, recess 17, nub 66 and slots 64 and 62 can be dimensioned to control the movement and timing of the cam followers 51a and 51b. For example, it is envisioned that the stages 64a, 64b and 62a and 62b can be dimensioned to control the timing and movement of the first and second retractors which, in turn, can effect the efficiency of the anastomosis.

Elongated stop 65 is preferably affixed to the distal end of cam 60 and rests atop the second retractor 50. Elongated stop 65 includes a distal end 69 and a proximal end 67 which includes two extending portions 67a and 67b each having an aperture 63a and 63b, respectively, disposed therethrough. Preferably, end 69 of stop 65 is sufficiently dimensioned such that it engages a corresponding biasing post 102 located within the SULU 100.

Preferably, the second retractor 50, the cam 60 and the elongated stop 65 are pre-assembled prior to insertion into the first retractor 80. More particularly and as best illustrated in FIGS. 10-12, elongated stop 65 is positioned atop arm 52 of the second retractor 50 between T-shaped heel section 56 and end 53. Apertures 63a and 63b of stop 65 align with aperture 61 of cam 60 such that once the cam 60 and the elongated stop 65 are inserted within slot 91 of the first retractor 80, pin 54 locks the two components 65 and 60 together through slot 85.

Cam 60 is positioned between the extending fins 58a and 58b of the second retractor 50 such that, when the retractor 50 and cam 60 are inserted within slot 91 of the first retractor, followers 51a and 51b are inserted through slot 87 and slot 89, respectively, and slideably couple the two components 50 and 60 within the first retractor 80. Handle lock 40 is then positioned atop the first retractor 80 as described above. First retractor 80 is then mounted on ribs 25a and 25b of housing 26 and cover plate 90, respectively, and tab 30 along with sliding sleeve 32 are engaged thereon. Handle 12 and lever 16 are then assembled as described above and pivotably mounted about post 21. Spring 70 is then positioned accordingly so as to bias handle 12 against housing 26.

Figure 24C:
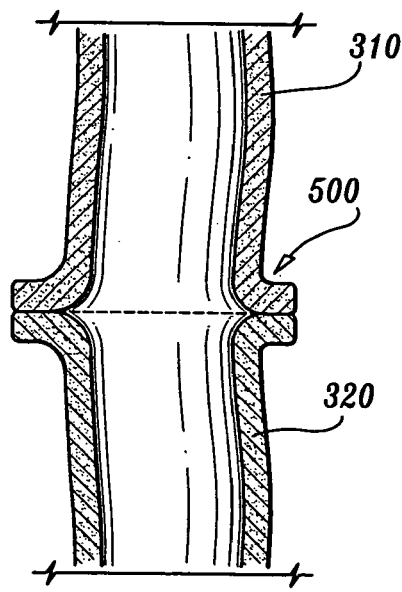
FIG. 24C is an enlarged, schematic view of a completed end-to-end anastomosis utilizing the presently disclosed surgical instrument showing an eversion on the exterior of the luminal structures.
Figure 24B:
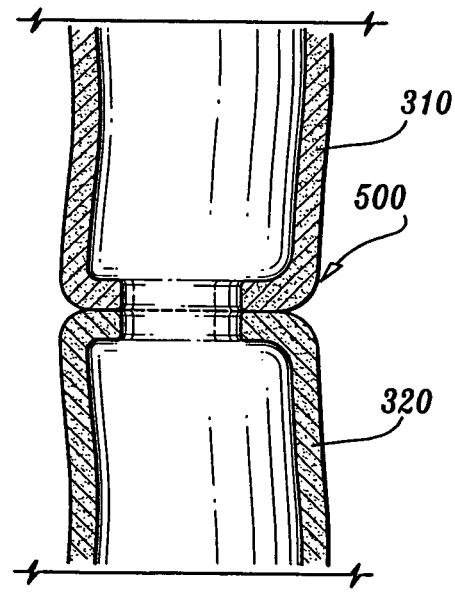
FIG. 24B is an enlarged, schematic view of a completed end-to-end anastomosis utilizing a prior art device showing an eversion on the interior of the luminal structures.
Figure 24A:
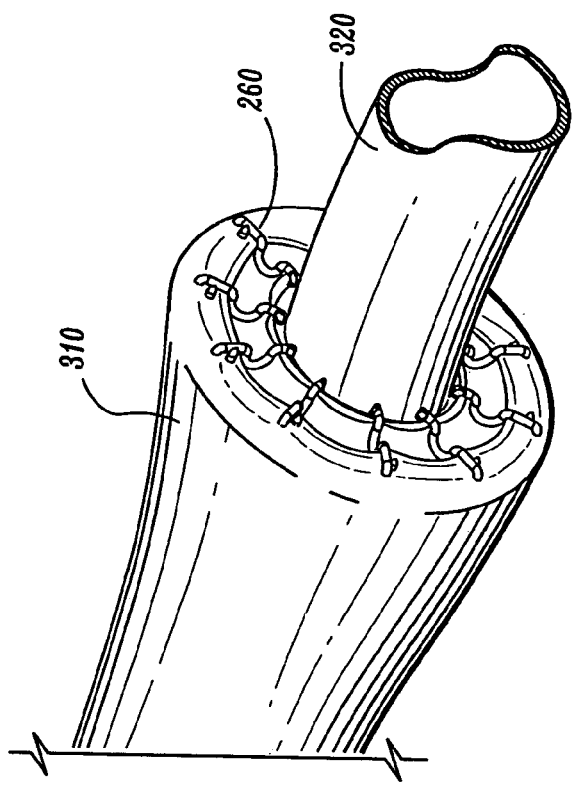
FIG. 24A is a view showing a completed end-to-end anastomosis.
Figure 24D:
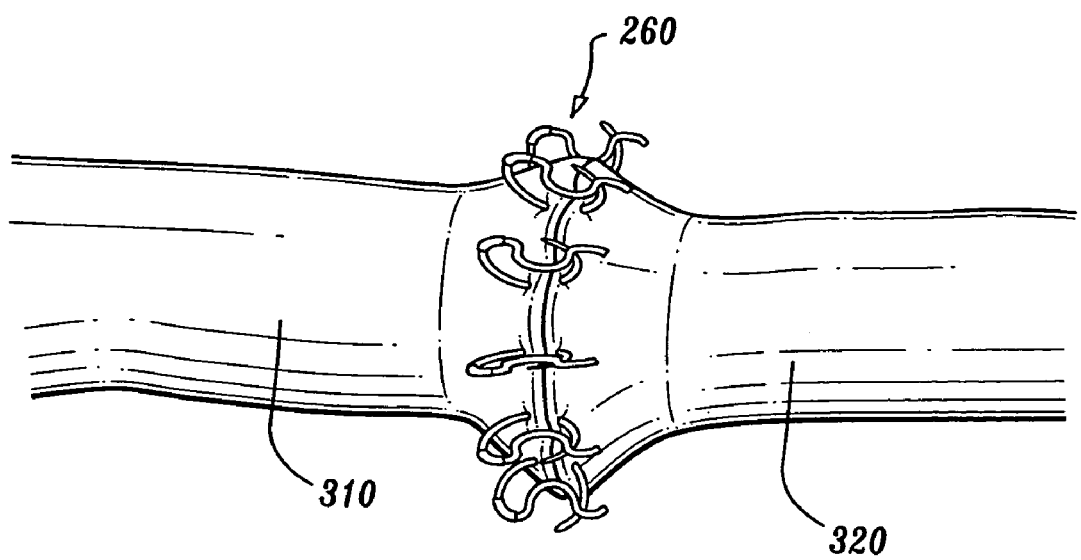
FIG. 24D is side view of a completed end-to-end anastomosis utilizing the presently disclosed surgical instrument.

Turning now to FIGS. 7-9 which show an exploded view of the internal working components of the SULU 100 which as mentioned above includes first retracting sleeve 110 and second retracting sleeve 120 which cooperate to deform fasteners 260 and securely fasten the two luminal structures 320, 310 in fluid communication as shown in FIGS. 24A and 24D.

More particularly and as best seen in FIGS. 7-7D, first retracting sleeve 110 includes a tube-like base 110a and an arcuate sleeve cap 110b which together define the first retracting sleeve 110. Base 110a includes a circular lip 112 located at its proximal end and a semi-circular anvil 118a located at the opposite end. A locking tab 116a having an elongated slit 182a located therein is disposed between lip 112 and anvil 118a. A longitudinally-extending slot 114a is disposed between the lip 112 and the locking tab 116a. At least one interface 117a downwardly depends from base 110a to mechanically engage a corresponding mechanical interface 117b disposed on sleeve cap 110b (FIG. 7). A flange 113a is preferably disposed beneath slot 114a and is sufficiently dimensioned to engage corresponding flanges $113b_1$ and $113b_2$ located on sleeve cap 110b. Slot 114a is sufficiently dimensioned to receive a tab 138a (FIG. 13) which projects from an upper surgical fastener support 130a which is explained in more detail below.

Sleeve cap 110b includes a semi-circular anvil 118b and a bifurcated proximal end 113 composed of flanges $113b_1$ and $113b_2$ which together define a slot 114b for receiving a tab 138b which projects from a lower surgical fastener support 130b which is explained in more detail below. Sleeve cap 110b also includes mechanical interfaces 117b which couples with corresponding mechanical interfaces 117a disposed on base 110a to engage sleeve cap 110b with base 110a. A locking tab 16b having an elongated slit 182b located therein is disposed between proximal end 113 and anvil 118b. A longitudinally-extending opening 111b is preferably disposed proximate locking tab 116b and aligns with a corresponding opening 111a in base 110a (FIG. 7C) such that the first luminal structure 320 can be received therethrough as seen best in FIGS. 17 and 18.

FIGS. 2A and 7D show a greatly enlarged view of anvil 118a which includes a semi-annular array of fastener support channels or cradles 119a each configured and dimensioned to support a surgical fastener 260 therein. Sleeve cap 110b also includes fastener support channels 119b which, when base 110a and sleeve cap 110b are assembled, align to form a circular array about the internal surfaces of anvil 118a and 118b. It is envisioned that anvils 118a and 118b can be designed to support different arrays of surgical fasteners 260 depending upon a particular purpose. Each channel 119a and 119b is preferably separated by an anchor 187a and 187b (FIG. 7) which releasably retains a projecting finger 124a, 124b of second retracting sleeve 120 (FIG. 2A).

Support channels 119a and 119b each include proximal ends 186a and 186b and distal ends 184a and 184b which are radially offset from one another to seat surgical fastener 260 within channels 119a and 119b in a radially offset manner the purpose of which will be explained below with respect to the operation of the surgical instrument 10. The distal end 184a of each channel 119a is preferably arched so as to correspond to the arcuate shape of the end of the surgical fastener 260 as best seen in FIG. 13A. It is anticipated that arching the distal end 184a will cause the surgical fastener 260 to deform upwardly and proximally upon retraction of the first retracting sleeve 110 by the first retractor 80 as explained below with reference to FIGS. 21-22.

FIGS. 7-7D also show second retracting sleeve 120 which includes an upper cuff 120a, a lower cuff 120b and an outer cap 128 which together define the second retracting sleeve 120. More particularly, upper cuff 120a includes a semi-annular lip 122a at one end and a plurality of retention fingers 124a at the opposite end. Upper cuff 120a also includes a first slot 101 which preferably aligns with slot 114a of the first retracting sleeve 110a to receive tab 138a of upper fastener support 130b therethrough. A second slot 126a receives locking tab 116a when cuff 120a is slideably mounted atop base 110a. Interfaces 129a mechanically engage corresponding interfaces 129b located on lower cuff 120b.

Lower cuff 120b includes a bifurcated proximal end 107 which comprises flanges 107b$_1$ and 107b$_2$ which define a slot 108 for receiving tab 138b of lower fastener support 130b therethrough and a plurality of retention fingers 124b which extend from the opposite end thereof. A slot 126b is disposed between the flanges 107b$_1$, 107b$_2$ and the fingers 124b for receiving locking tab 116b of the sleeve cap 110b when cuff 120b is slideably mounted thereon. A longitudinally-extending opening 121b is disposed proximate slot 126b and aligns with a corresponding opening 121a in upper cuff 120a and also aligns with openings 111a and 111b of the first retracting sleeve 110 such that the first luminal structure 320 can be received therethrough as seen best in FIGS. 17 and 18.

A semi-circular cuff cap 128 is disposed atop lower cuff 120b and mechanically interfaces with upper cuff 120a such that semi-circular lips 122a and 122b form circular lip 122. More particularly, cuff cap 128 includes a plurality of detents 123b which mechanically engage a corresponding plurality of notches 123a located in upper cuff 120a such that the cuff cap 128, upper cuff 120a and lower cuff 120b all move in unison upon retraction of the second retracting sleeve 120. Sleeve cap 128 is preferably bifurcated at its distal end forming slot 109 which is dimensioned to receive tab 138b.

As can be appreciated, fingers 124a and 124b move upon retraction of the second retracting sleeve 120 to release the surgical fasteners 260 after firing. More particularly and as best seen in FIGS. 2A and 7A, the distal end of each finger 124a is forked and includes a first prong 127a which retains a surgical fastener 260 within the fastener support channels 119a and a second prong 125a which interlocks with anchor 187a to releasably lock the finger 124a to the first retracting sleeve 110 until released by the second retractor 50 (FIGS. 22A and 22B) which will be explained in more detail with respect to the operation of the surgical instrument 10. Likewise, each finger 124b of lower cuff 120b includes prongs 127b and 125b which operates in the same manner.

As mentioned previously, the SULU 100 also includes fastener support 130 which has an upper support 130a and a lower support 130b which, when assembled, internally house the first and second retracting sleeves 110 and 120, respectively, along with their individual working components. Upper support 130a and lower support 130b each include a distal end 135a and 135b each having an array of braces 137a and 137b, respectively, which project radially from distal ends 135a and 135b. As best illustrated in FIG. 2, each brace 137a and 137b supports an upwardly extending support leg 262 of a surgical fastener 260 disposed within one of the channels 119a or 119b. A plurality of radially extending slots 139a and 139b are disposed between each support brace 137a, 137b for retaining a surgical fastener 260 therein and for restricting unwanted lateral movement of each fastener 260. It is anticipated that each surgical fastener 260 is positioned within a slot 139a, 139b such that convexity 263 projects outwardly from brace 137a, 137b and, after anastomosis, cooperates with the base leg 264 to retain the two luminal structures 32- and 310 in close abutment against one another (FIGS. 21B, 24A and 24D).

Upper support and lower support 130a and 130b, respectively, also include hinges 136a and 136b which, when the SULU 100 is assembled, matingly engage one another to allow pivotable movement between the supports 130a and 130b from an open position (FIG. 23) to a closed position (FIG. 2). Preferably, a pin 180 secures the two hinges 136a and 136b together (FIG. 6). Upper and lower supports 130a and 130b each include a longitudinally-extending opening 133a (FIG. 23) and 133b which aligns with openings 121a, 121b, 111a and 111b described above to receive the first luminal structure 320 therethrough as seen best in FIGS. 17 and 18. Longitudinally oriented slots 131a and 131b are disposed adjacent openings 133a and 133b on the upper and lower support members 130a and 130b, respectively, for receiving locking tabs 116a and 116b in much the same manner as described above with respect to slots 126a and 126b of the second retracting sleeve 120.

Lower support 130b includes a pair of shoulders 132a and 132b disposed on opposite sides of opening 133b for slideably receiving a corresponding pair of flanges 144a and 144b associated with an upper locking sleeve 140a. More particularly, each flange 144a and 144b extends distally from the upper locking sleeve 140a to define a notch 149a and 149b, respectively, therein for receiving shoulders 132a and 132b of lower support 130b.

Figure 23:
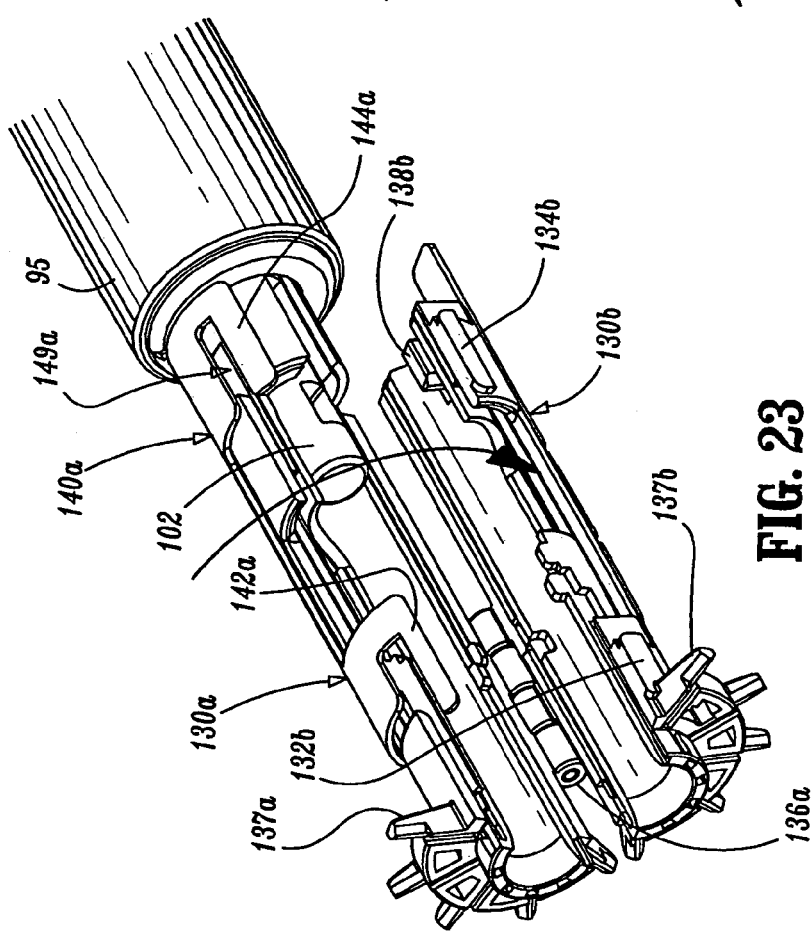
FIG. 23 is a perspective view of the SULU showing the pivotable movement of the two supports which open after firing to release the first luminal structure.

Upper locking sleeve 140a includes a C-shaped clip 146a (FIG. 8) disposed therein which has pair of opposing hooks 147a for snap-lockingly engaging slit 182a of locking tab 116a of first retracting sleeve 110. A lower locking sleeve 140b operates in a similar manner and includes a pair of opposing hooks 147b for snap-lockingly engaging slit 182b of locking tab 116b of first retracting sleeve 110. Upper locking sleeve 140a also includes an opening 141a which aligns with openings 133a, 133b, 121a, 121b, 111a and 111b described above to receive the first luminal structure 320 therethrough as seen best in FIGS. 17 and 18. It is envisioned that upon retraction of the second retracting sleeve 120, upper locking sleeve 140a will move proximally relative to shoulders 132b and 134b and disengage shoulders 132a, 132b which, in turn, will allow the upper and lower supports 130a and 130b to pivot about pin 180 and release the first luminal structure 320 (FIGS. 21E and 23). This will be explained in greater detail with respect to the operation of the instrument as described below.

SULU 100 also includes a biasing post 102 which mechanically aligns upper and lower supports 130a and 130b in fixed relation relative to one another. More particularly, biasing post 102 includes a proximal end 103 and a distal end 105 and has a vertically oriented cavity 106 disposed therethrough for receiving tabs 138a and 138b of the upper and lower supports 130a and 130b, respectively. As mentioned above, tabs 138a and 138b pass through slots 114a, 114b of the first retracting sleeve 110 and through slots 101, 108 and 109 of the second retracting sleeve 120 and mechanically align with one another within cavity 106 as best seen in FIG. 21B.

Turning now in detail to the loading of the SULU 100 within actuator assembly 20 as best seen in FIG. 5, thumb tab 30 is moved proximally byway of thumb guide 35 against spring 38 which, in turn, moves sleeve 32 and protective cover 95 proximally to expose carriages 86 and 88. The SULU 100 is then loaded within actuator assembly 20 by placing lip 112 within carriage 88 and lip 122 within carriage 86. As best shown in FIG. 13, lip 122 is positioned near the distal end of carriage 86 which allows lip 122 and, hence, second retracting sleeve 120, to move independently from the first retracting sleeve upon activation of the second retractor 50. In contrast, carriage 88 is dimensioned smaller than carriage 86 such that lip 112 fits snugly within carriage 88. Once the SULU is positioned within carriages 86 and 88, thumb tab 30 is released and spring 38 biases sleeve 32 and protective cover 95 distally over lips 112 and 122 to lock the SULU 100 within the actuator assembly 20.

In use and as shown in FIGS. 17-24D, the user inserts a free end 322 of the first luminal structure, e.g., intestine, into opening 133 of the SULU and pulls via a surgical hook or graspers the free end 322 towards the distal end of the SULU 100. The user then everts the first luminal structure 320 over the anvils 118a, 118b of the SULU 100 such that the free end 322 is retained by end 269 of the surgical fasteners 260 (see FIG. 19B). Everting of the first luminal structure 320 may be achieved by any suitable known instruments and/or techniques such as by using graspers. The first luminal structure 320 is preferably everted over the full length of the base leg 264 such that the first luminal structure 320 resides in close proximity to convexity 263 as best seen in FIG. 19B.

Figure 20:
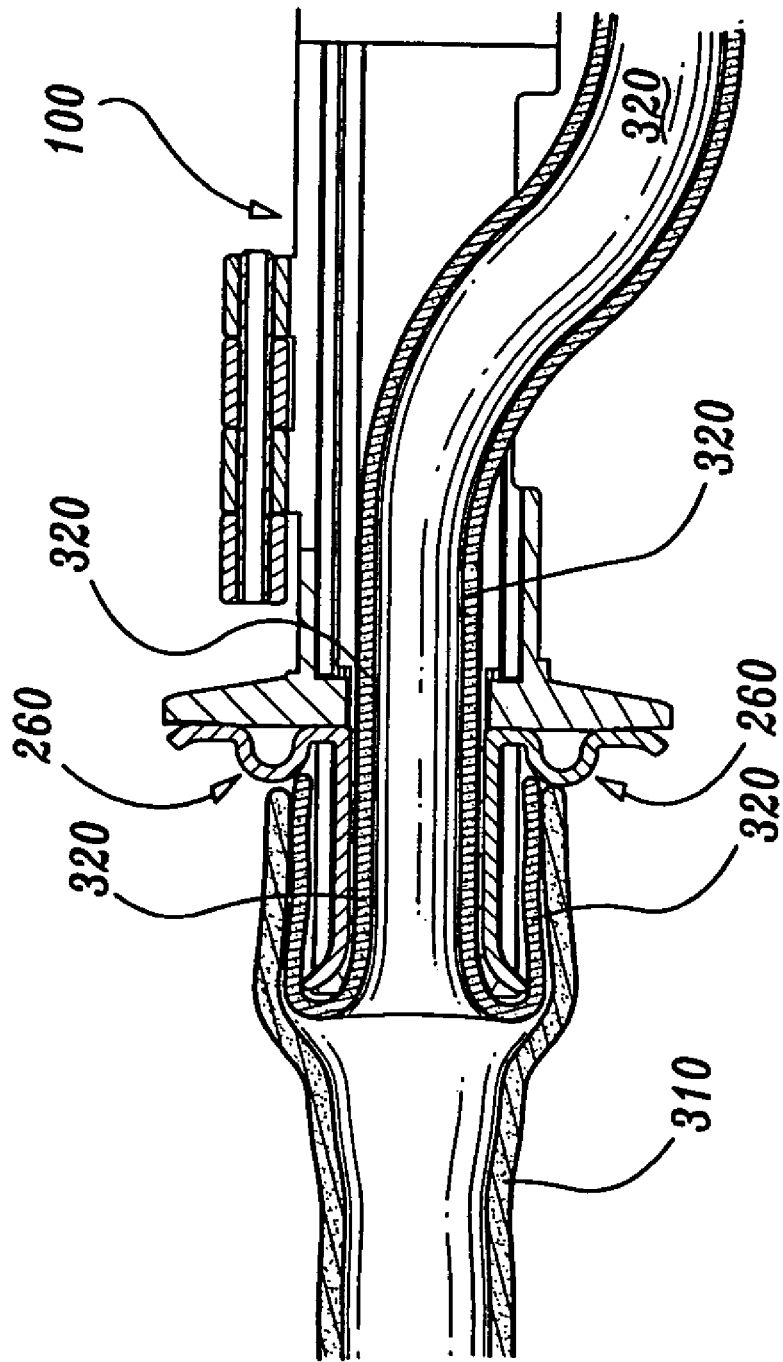
FIG. 20 is a side cross-sectional view showing the first and second luminal structures in position atop the distal end of the SULU prior to activation of the actuator.

The first luminal structure 320 is then secured to the distal end of the SULU 100 by a suture or other convention means or by virtue of an additional securing mechanism (not shown) disposed on the SULU 100. The user then inserts the end of the SULU 100 and the first luminal structure 320 into the second luminal structure 310 such that the distal end 269 of each of the plurality of fasteners 260 and the everted end portions 322 of the first luminal structure 320 are sufficiently inserted into end 312 (FIGS. 18 and 20A). As seen best in the enlarged view of FIG. 20, the support leg 262, convexity 263 and prong 267 of each surgical fastener 260 remains outside incision 312. The instrument is now preset for firing.

FIGS. 21-22 show the firing sequence of instrument 10, i.e., when the handle 12 is depressed by the user. As best shown in FIGS. 21 and 21A, as handle 12 is depressed downwardly in the direction of reference arrow "A", lever 16 simultaneously imparts movement to both handle lock 40 and cam 60. More particularly, downward movement of handle 12 causes flanges 14a and 14b of lever 16 to urge flanges 42a and 42b of handle lock 40 distally against spring 45 in the direction of reference arrow "B" (FIG. 21). At the same time, handle 12 causes recess 17 of lever 16 to bias nub 66 which, in turn, causes cam 60 to deflect downwardly and proximally as best seen in FIG. 21A. Preferably, recess 17 in lever 16 is dimensioned to control the specific movement of nub 66 within recess 17 which, in turn, controls the overall movement of cam 60. Downward and proximal movement of cam 60 causes cam followers 51a and 51b to move within the first cam stages 64a and 62a of slots 64 and 62, respectively, which, in turn, moves the first retractor 80 and protective cover 95 proximally in the direction of reference arrow B'.

As seen best in FIG. 21, as retractor 80 moves proximally as a result of the movement of cam followers 51a and 51b within slots 64 and 62, slot 85 moves proximally until it abuts pin 54. Preferably, when slot 85 abuts pin 54, cam 60 is forced more downwardly about pin 54 such that cam followers 51a and 51b move more proximally to engage the second stages 64b and 62b of the cam slots 64 and 62, respectively.

Figure 22A:
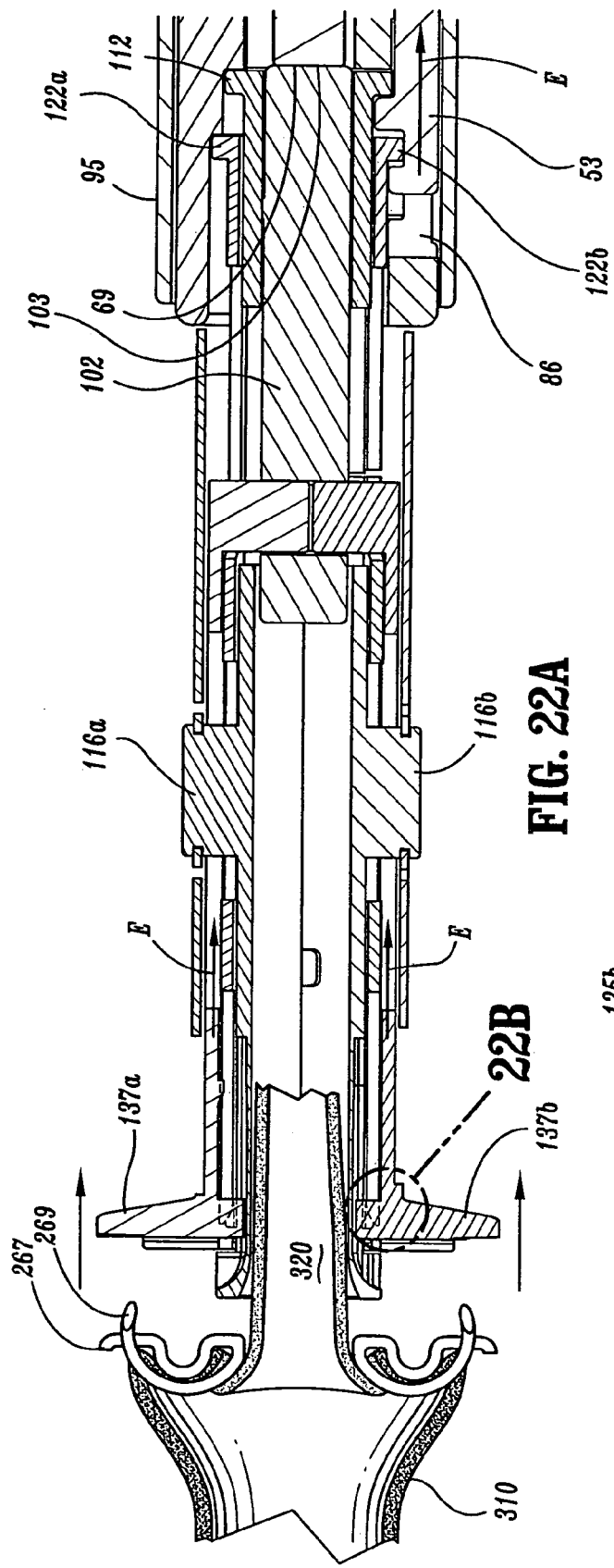
FIG. 22A is a side cross-sectional view of the SULU during the second firing stage and showing the movement of a second retracting sleeve which moves as a direct result of the movement of the second retractor to release the surgical fasteners.
Figure 22B:
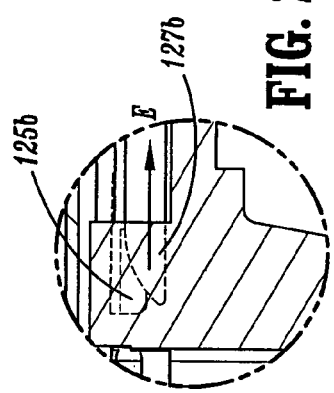
FIG. 22B is a greatly enlarged side cross-sectional view showing the retracting movement of a finger-like retention prong which moves as a direct result of the movement of the second retractor.
Figure 26:
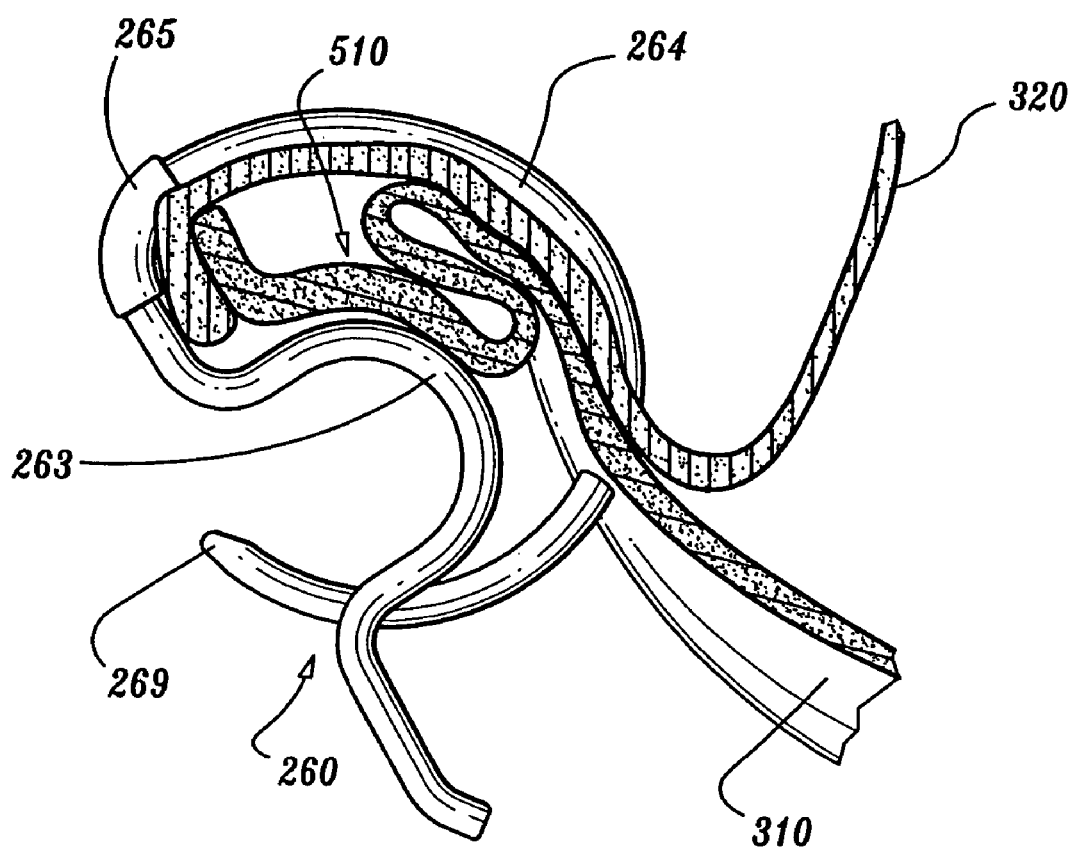
FIG. 26 is an enlarged cross-section showing the ends of the two luminal structures after anastomosis and engaged between the surgical fastener.

As mentioned above, the first retractor 80 retracts the first retracting sleeve 110 (FIG. 21) which, in turn, causes surgical fasteners 260 to deform as shown in FIGS. 21B and 21D. More particularly and as best shown in FIG. 21B, proximal movement of the first retractor 80 causes both the first retracting sleeve 110 and the second retracting sleeve 120 to move proximally relative to biasing post 102 until biasing post 102 abuts the end 69 of elongated stop 65. As a result, anvils 118a and 118b deform the distal ends 269 of surgical fasteners 260 upwardly and proximally towards braces 137a and 137b, respectively, i.e., arc-like distal ends 184a and 184b cause surgical fasteners 260 to deform upwardly and proximally upon retraction of the first retracting sleeve 110. At the same time, the second luminal structure 310 is forced slightly proximally and extending prongs 267 penetrate to hold the second luminal structure 310 in position as best seen in FIG. 22A. FIG. 26 illustrates the resulting deformation of clip 260 through the two luminal structures 320 and 310.

It is anticipated that the radially offset orientation of the opposite ends 186a, 186b and 184a, 184b of the support channels 119a and 119b, respectively will cause the opposite ends 267 and 269 of the surgical fasteners 260 to deform at an angle relative to one another as best shown in FIG. 21D. This allows end 269 to deform proximal to braces 137a and 137b. Preferably, braces 137a and 137b have a tapered cross section to deform end 269 of surgical fastener 260 radially from end 267 during deformation.

It is anticipated that the presently disclosed surgical fasteners 260 can also include an end 269 which is blunt and which does not penetrate the luminal structures 320 or 310 upon deformation. As can be appreciated, this offers the user the option of performing a less traumatic anastomosis.

FIG. 21C shows the resulting position of the spacer 104 of the biasing post 102 after the first retractor 80 retracts the first and second retracting sleeves 110 and 120, respectively. More particularly, spacer 104 frictionally locks the first retracting sleeve 110 relative to the second retracting sleeve 120 and prevents the first retracting sleeve 110 from recoiling after firing.

FIG. 21E shows the proximal movement of the locking sleeve 140a as a result of the movement of the first retracting sleeve 110. More particularly, when the first retracting sleeve 110 is retracted proximally, locking tab 116a retracts within slot 131a of support 130a and biases locking sleeve 140a in a proximal direction as well as seen by reference arrow "C". Proximal movement of the locking sleeve 140a relative to support 130a disengages flanges 142a and 144a from shoulders 132b and 134b, respectively, of support 130b which, in turn, unlocks supports 130a and 130b from one another thus permitting pivotal movement of the support members 130a, 130b as best seen in FIGS. 21E and 23.

Continued downward movement of handle 12 results in both proximal movement of the second retractor 50 and engagement of the handle lock 40 with the handle 12. More particularly and as best illustrated in FIG. 22, as the user continues to move the handle 12 in a downward direction, flanges 14a and 14b clear corresponding flanges 42a and 42b and spring 45 biases handle lock 40 proximally in the direction of reference arrow "D" to lock the handle 12 in position. Simultaneously, cam 60 is rotated about pin 54 to a point where the second stages 64a and 62a of the cam slots 64 and 62 effect the movement of the cam followers 51a and 51b. More particularly, as cam 60 is forced downwardly, the second stage 62a of cam slot 62 moves cam follower 51b proximally which, in turn, moves the second retractor 50 proximally. The second stage 64a of cam slot 64 is generally vertically oriented and, as a result, cam follower 51a moves vertically upon continued downward movement of handle 12. Slot 57 of retractor 50 allows the second retractor 50 to slide proximally relative to cam follower 51a.

As mentioned above, second retractor 50 moves the keylike end 53 of the second retracting sleeve 120 within carriage 86 relative to the first retracting sleeve 110 as illustrated by reference arrow "E" of FIG. 22A. Proximal movement of the second retracting sleeve 120 retracts the prongs 127a and 127b of fingers 124a, 124b, respectively, which releases the surgical fasteners 260 as illustrated by reference arrow "E" of FIG. 22B.

It is envisioned that the surgical instrument 10 and/or the SULU 100 may need to be manipulated to assure consistent and tactful release of the surgical fasteners 260 from the SULU. For example, it is contemplated that after and/or simultaneously with activation of the handle 12, the presently disclosed methods described herein may include the step of manipulating the surgical instrument 10 or SULU 100 relative to the surgical fasteners 260 to facilitate release thereof, e.g., rotational or off-axis manipulation relative to axis "A" (See FIG. 5), vertical manipulation, horizontal manipulation, pivotal manipulation and/or any simultaneous or sequential combination of these aforedescribed manipulative movements.

Further, it is contemplated that the surgical instrument 10 or the SULU 100 may be manufactured to include an additional activator, lever, handle, pivot element, linkage or the like (not shown) which upon activation thereof will manipulate the surgical instrument 10 and/or SULU 100 relative to the surgical fasteners 260 in one of the manners described above to facilitate consistent and tactful release of the surgical fasteners 260.

As mentioned above, after sleeve 110 is retracted, locking sleeve 140a moves proximally to allow the two supports 130a and 130b to pivot away from one another as shown in FIG. 23 to permit the removal of the intestine 320 from within the SULU thereby completing the end-to-end anastomosis as shown in FIGS. 24A and 24D. FIG. 26 illustrates a side view of the resulting deformation of surgical fastener 260 through the two luminal structures 320 and 310. As can be appreciated, the deformation of the surgical fastener 260 forms a series of folds 510 in the tissue 310 which help maintain the anastomosis.

Figure 25A:
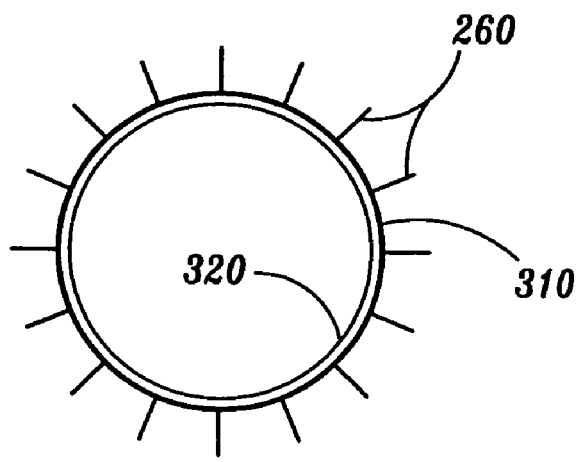
FIG. 25A is a view showing the surgical fastener staple pattern of the instrument described with respect to FIGS. 1-24C.
Figure 25B:
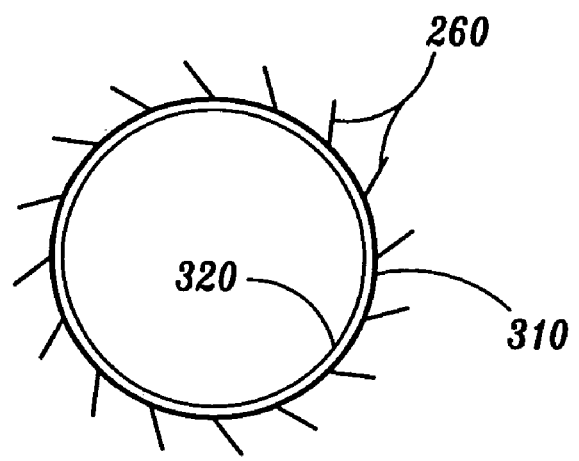
FIG. 25B. is a view showing one possible alternative surgical fastener staple pattern.

FIG. 25A shows a schematic diagram of the surgical fastener staple pattern which is formed upon actuation of the instrument described above with respect to FIGS. 1-25B. More particularly, the surgical fasteners are supported by the fastener support braces 137a, 137b in a normal manner relative to a longitudinal axis "A" (FIG. 5) extending through the SULU. It is envisioned that other surgical fastener staple patterns, e.g., spiral, tangential or angular relative to axis "A", may be utilized to achieve hemostasis between luminal structures (FIG. 25B). For example, it is contemplated that arranging the surgical fasteners 260 in one of the aforedescribed patterns may enable more surgical fasteners 260 to be employed within the same spatial considerations which may achieve a more consistent and/or more reliable hemostasis between luminal structures 320, 310.

As can be appreciated, the presently disclosed instrument and method as described herein allows the user to perform an end-to-end anastomosis deep within the colon or small intestine without the need for a gastrotomy and/or other procedures necessary for the proper insertion of the surgical instrument. For example, the presently disclosed instrument 10 may be particularly useful in low anterior resection of the colon whereas prior devices and techniques normally require complex manipulation and positioning of the instrument to reach the low anterior section of the colon and to successfully complete the anastomosis. In many cases, open surgical conditions were required to access the surgical area and properly manipulate the instrument for stapling.

As can be appreciated, the a large majority of the prior art end-to-end anastomosis devices produce an eversion 500 which is interior to the lumen, e.g., colon, which may cause fibrin stenosis at the anastomosis site requiring further resection and/or other operative measure to resolve the condition (see FIG. 24B). The presently disclosed instrument and method described herein produces an eversion 500 which is exterior to the colon which reduces the likelihood of stenosis at the site (see FIG. 24C). Further, a number of known end-to-end anastomotic devices include a knife-like assembly which cuts away healthy tissue beyond the anastomosis to complete the anastomosis. As can be appreciated, the presently disclosed instrument does not include a knife (or the like) to complete the anastomosis hence reducing the amount of healthy tissue lost during the anastomosis.

It will be understood that various modifications may be made to the embodiment shown herein. For example, the instrument may be sized to perform an anastomosis for other vessels and luminal tissue. Moreover, although the various internal components of the instrument 10 are shown engaged by particular mechanical interfaces it is envisioned that other types of mechanical interfaces can be employed to achieve the same or similar purpose, e.g., snap-fit, tongue and groove, press fit, etc. Therefore, the above description should not be construed as limiting, but merely as exemplifications of preferred embodiment. Those skilled in the art will envision other modifications within the scope and spirit of the claims appended hereto.

What is claimed:

1. A surgical instrument for performing an end-to-end anastomosis of first and second luminal structures, comprising:
    a housing having an actuator attached thereto;
    a selectively removable loading unit attached to a distal end of the housing, the loading unit configured to releasably support a plurality of surgical fasteners in an array-like fashion at a distal end thereof, the plurality of surgical fasteners being simultaneously deformable upon activation of the actuator such that a distal end of each of the plurality of surgical fasteners secures a distal end of each luminal structure to complete the end-to-end anastomosis wherein the resulting eversion is exterior to the luminal structures.

2. A surgical instrument according to claim 1 wherein the distal end of at least one of the plurality of surgical fasteners penetrates an end of at least one of the luminal structures.

3. A surgical instrument according to claim 1 wherein at least one of the plurality of surgical fasteners includes a convexity and a base leg which cooperate after deformation of the at least one of the plurality of surgical fasteners to securely retain the two luminal structures in close abutment with one another.

4. A surgical instrument according to claim 1 wherein at least one of the plurality of surgical fasteners includes a base leg and a proximal portion such that, upon deformation, the base leg of the at least one of the plurality surgical fasteners deforms at an angle relative to the proximal portion of the at least one of the plurality of surgical fasteners.

5. The surgical instrument according to claim 1 wherein the distal end of the selectively removable loading unit includes an anvil which releasably supports the distal end of the at least one of the plurality of surgical fasteners and supports an everted end of the first luminal structure.

6. The surgical instrument according to claim 5 wherein the anvil includes an angled surface which deforms the plurality of surgical fasteners proximally during actuation.

7. The surgical instrument according to claim 1 wherein the distal end of the selectively removable loading unit includes a plurality of elongated channels defined therein which support a corresponding plurality of the surgical fasteners, each of the plurality of elongated channels includes a distal end and a proximal end, each distal end of each elongated channel being radially offset from each proximal end of each elongated channel such that the proximal and distal ends of each of the plurality surgical fasteners are supported in a radially offset manner relative to one another.

8. The surgical instrument according to claim 1 wherein at least one of the plurality of surgical fasteners includes a base leg and an upwardly extending support leg including a blunt prong at a free end thereof, the blunt prong being configured to hold the luminal structures in position after actuation.

9. The surgical instrument according to claim 1 wherein the selectively removable loading unit includes a longitudinal axis defined therethrough and the plurality of surgical fasteners are supported in the distal end of the selectively removable loading unit in a substantially normal configuration relative to the longitudinal axis.

10. The surgical instrument according to claim 1 wherein the selectively removable loading unit includes a longitudinal axis defined therethrough and the plurality of surgical fasteners are supported in the distal end of the selectively removable loading unit in a substantially tangential configuration relative to the longitudinal axis.

11. The surgical instrument according to claim 1 wherein the selectively removable loading unit includes a longitudinal axis defined therethrough and the at least one of the plurality of surgical fasteners are supported in the distal end of the selectively removable loading unit in a substantially normal configuration relative to the longitudinal axis and at least one of the plurality of surgical fasteners are supported in the distal end of the selectively removable loading unit in a substantially tangential configuration relative to the longitudinal axis.

12. A surgical instrument for performing an end-to-end anastomosis of first and second luminal structures, comprising:

a housing having at least one actuator attached thereto and a loading tab, the loading tab being configured to move from a first configuration for operatively coupling a selectively removable loading unit to a distal end of the housing to a second position for securing the selectively removable loading unit to a distal end of the housing;

a plurality of surgical fasteners releasably supportable in an array-like fashion in a distal end of the selectively removable loading unit, the plurality of surgical fasteners being simultaneously deformable upon activation of the actuator such that a distal end of each of the plurality of surgical fasteners secures a distal end of each luminal structure to complete the end-to-end anastomosis wherein the resulting eversion is exterior to the luminal structures.

13. The surgical instrument according to claim 12 wherein the actuator includes a cam member having two cam followers which ride along two cam slots defined within the cam member.

14. The surgical instrument according to claim 13 wherein the selectively removable loading unit includes two halves which are pivotable relative to one another.

15. The surgical instrument according to claim 14 wherein one of the cam slots includes two cam stages, a first stage for retracting a first retracting sleeve of the selectively removable loading unit to simultaneously deform the plurality of surgical fasteners and a second stage for retracting the first retracting sleeve relative to a second retracting sleeve of the selectively removable loading unit to unlock the two halves of the selectively removable loading unit after anastomosis.

* * * * *